US012605702B2

(12) United States Patent
Conley et al.

(10) Patent No.: US 12,605,702 B2
(45) Date of Patent: Apr. 21, 2026

(54) MEASURING AND/OR DETECTING ANALYTES IN URINE, AND ASSOCIATED SYSTEMS, DEVICES, AND METHODS

(71) Applicant: REPRIEVE CARDIOVASCULAR, INC., Milford, MA (US)

(72) Inventors: Eric Conley, York, ME (US); Jim Dillon, South Kingstown, RI (US); Howard Robert Levin, Teaneck, NJ (US); Zoar Engelman, New York, NY (US); Martin Peacock, Horten (NO); Megha Shah, Milford, MA (US); Andrew Victor Halpert, Brookeline, MA (US)

(73) Assignee: REPRIEVE CARDIOVASCULAR, INC., Milford, MA (US)

( * ) Notice: Subject to any disclaimer, the term of this patent is extended or adjusted under 35 U.S.C. 154(b) by 834 days.

(21) Appl. No.: 17/660,778

(22) Filed: Apr. 26, 2022

(65) Prior Publication Data

US 2022/0339622 A1 Oct. 27, 2022

Related U.S. Application Data

(60) Provisional application No. 63/203,818, filed on Jul. 30, 2021, provisional application No. 63/179,975, filed on Apr. 26, 2021.

(51) Int. Cl.
    B01L 3/00 (2006.01)
    G01N 33/493 (2006.01)

(52) U.S. Cl.
    CPC ............ B01L 3/502 (2013.01); G01N 33/493 (2013.01); *B01L 2200/04* (2013.01); *B01L 2300/0663* (2013.01); *B01L 2400/0655* (2013.01)

(58) Field of Classification Search
    CPC ................ B01L 3/502; B01L 2200/04; B01L 2300/0663; B01L 2400/0655; B01L 3/502715; G01N 33/493
    See application file for complete search history.

(56) References Cited

U.S. PATENT DOCUMENTS 3,954,010 A    5/1976  Hilblom
4,132,644 A    1/1979  Kolberg
               (Continued)

FOREIGN PATENT DOCUMENTS

EP        0258690       3/1998
EP        1986007 A1   10/2008
          (Continued)

OTHER PUBLICATIONS

U.S. Appl. No. 16/544,975, filed Aug. 20, 2019, Levin.
(Continued)

*Primary Examiner* — Samuel P Siefke
(74) *Attorney, Agent, or Firm* — Perkins Coie LLP

(57) ABSTRACT

The present technology is generally directed to flow cartridges configured to measure and/or detect analytes in urine. A representative flow cartridge includes a urine inlet configured to receive urine from a patient, a flow channel fluidly coupled to the urine inlet, and sensors fluidly coupled to the flow channel that are configured to measure parameters of the urine flow. The sensors are aligned with corresponding sensing zones of the flow channel and are operable to generate sensor data based on urine flow through the sensing zones. In some embodiment, the sensor data is used to provide fluid therapy to the patient by adjusting an amount or rate of diuretic and/or hydration fluid based on the sensor data.

20 Claims, 6 Drawing Sheets

(56) References Cited

U.S. PATENT DOCUMENTS

| | | | |
|---|---|---|---|
| 4,146,029 A | 3/1979 | Ellinwood, Jr. | |
| 4,204,957 A | 5/1980 | Weickhardt | |
| 4,216,462 A | 8/1980 | McGrath et al. | |
| 4,229,299 A | 10/1980 | Savitz et al. | |
| 4,261,360 A | 4/1981 | Perez | |
| 4,275,726 A | 6/1981 | Schael | |
| 4,291,692 A | 9/1981 | Bowman et al. | |
| 4,343,316 A | 8/1982 | Jespersen | |
| 4,411,649 A | 10/1983 | Kamen | |
| 4,448,207 A | 5/1984 | Parrish | |
| 4,449,538 A | 5/1984 | Corbitt et al. | |
| 4,504,263 A | 3/1985 | Steuer et al. | |
| 4,658,834 A | 4/1987 | Blankenship et al. | |
| 4,712,567 A | 12/1987 | Gille et al. | |
| 4,728,333 A | 3/1988 | Masse et al. | |
| 4,728,433 A | 3/1988 | Buck et al. | |
| 4,813,925 A | 3/1989 | Anderson, Jr. et al. | |
| 4,923,598 A | 5/1990 | Schal | |
| 4,994,026 A | 2/1991 | Fecondini | |
| 5,038,109 A | 8/1991 | Goble | |
| 5,098,379 A | 3/1992 | Conway et al. | |
| 5,176,148 A | 1/1993 | Wiest et al. | |
| 5,179,862 A | 1/1993 | Lynnworth | |
| 5,207,642 A | 5/1993 | Orkin et al. | |
| 5,573,506 A | 11/1996 | Vasko | |
| 5,586,973 A | 12/1996 | Lemaire et al. | |
| 5,709,670 A | 1/1998 | Vancaillie et al. | |
| 5,722,947 A | 3/1998 | Jeppsson et al. | |
| 5,769,087 A | 6/1998 | Westphal et al. | |
| 5,814,009 A | 9/1998 | Wheatman | |
| 5,891,051 A | 4/1999 | Han et al. | |
| 5,910,252 A | 6/1999 | Truitt et al. | |
| 5,916,153 A | 6/1999 | Rhea, Jr. | |
| 5,916,195 A | 6/1999 | Eshel et al. | |
| 5,981,051 A | 11/1999 | Motegi et al. | |
| 5,984,893 A | 11/1999 | Ward | |
| 6,010,454 A | 1/2000 | Arieff et al. | |
| 6,171,253 B1 | 1/2001 | Bullister et al. | |
| 6,231,551 B1 | 5/2001 | Barbut | |
| 6,272,930 B1 | 8/2001 | Crozafon | |
| 6,514,226 B1 | 2/2003 | Levin et al. | |
| 6,531,551 B2 | 3/2003 | Ohno et al. | |
| 6,537,244 B2 | 3/2003 | Paukovits et al. | |
| 6,554,791 B1 | 4/2003 | Cartledge et al. | |
| 6,640,649 B1 | 11/2003 | Paz et al. | |
| 6,740,072 B2 | 5/2004 | Starkweather et al. | |
| 6,752,779 B2 | 6/2004 | Paukovits et al. | |
| 6,796,960 B2 | 9/2004 | Cioanta et al. | |
| 6,827,702 B2 | 12/2004 | Lebel et al. | |
| 6,942,637 B2 | 9/2005 | Cartledge et al. | |
| 7,029,456 B2 | 4/2006 | Ware et al. | |
| 7,044,002 B2 | 5/2006 | Ericson et al. | |
| 7,086,615 B2 | 8/2006 | Joseph | |
| 7,137,964 B2 | 11/2006 | Flaherty | |
| 7,278,983 B2 | 10/2007 | Ireland et al. | |
| 7,727,222 B2 | 6/2010 | Da Silva | |
| 7,736,354 B2 | 6/2010 | Gelfand | |
| 7,739,921 B1 | 6/2010 | Babcock | |
| 7,758,562 B2 | 7/2010 | Gelfand | |
| 7,758,563 B2 | 7/2010 | Gelfand | |
| 7,837,667 B2 | 11/2010 | Gelfand | |
| 7,938,817 B2 | 5/2011 | Gelfand | |
| 8,007,460 B2 | 8/2011 | Gelfand | |
| 8,075,513 B2 | 12/2011 | Rudko et al. | |
| 8,233,957 B2 | 7/2012 | Merz et al. | |
| 8,444,623 B2 | 5/2013 | Gelfand | |
| 8,556,846 B2 | 10/2013 | O'Mahony et al. | |
| 8,714,030 B1 | 5/2014 | Liu | |
| 9,526,833 B2 | 12/2016 | Gelfand et al. | |
| 10,045,734 B2 | 8/2018 | Da Silva | |
| 10,537,281 B2 | 1/2020 | Thompson et al. | |
| 10,639,419 B2 | 5/2020 | Halpert | |
| 10,881,774 B2 | 1/2021 | Halpert | |
| 11,064,939 B2 | 7/2021 | Da Silva | |
| 11,213,621 B2 | 1/2022 | Halpert | |
| 11,357,446 B2 | 6/2022 | Levin et al. | |
| 11,633,137 B2 | 4/2023 | Conley et al. | |
| 11,696,985 B2 | 7/2023 | Halpert | |
| 11,950,925 B2 | 4/2024 | Levin | |
| 11,986,302 B2 | 5/2024 | Conley et al. | |
| 11,992,332 B2 | 5/2024 | Da Silva | |
| 2001/0029340 A1 | 10/2001 | Mault et al. | |
| 2002/0025597 A1 | 2/2002 | Matsuda | |
| 2002/0072647 A1 | 6/2002 | Schock et al. | |
| 2002/0107536 A1 | 8/2002 | Hussein | |
| 2002/0151834 A1 | 10/2002 | Utterberg | |
| 2002/0161314 A1 | 10/2002 | Sarajarvi | |
| 2003/0040700 A1 | 2/2003 | Hickle | |
| 2003/0048185 A1 | 3/2003 | Citrenbaum et al. | |
| 2003/0048432 A1 | 3/2003 | Jeng et al. | |
| 2003/0114786 A1 | 6/2003 | Hiller et al. | |
| 2004/0025597 A1 | 2/2004 | Ericson et al. | |
| 2004/0059295 A1 | 3/2004 | Cartledge et al. | |
| 2004/0081585 A1 | 4/2004 | Reid | |
| 2004/0087894 A1 | 5/2004 | Flaherty | |
| 2004/0122353 A1 | 6/2004 | Shahmirian et al. | |
| 2004/0133187 A1 | 7/2004 | Hickle | |
| 2004/0163655 A1 | 8/2004 | Gelfand et al. | |
| 2004/0167415 A1 | 8/2004 | Gelfand et al. | |
| 2004/0167464 A1 | 8/2004 | Ireland et al. | |
| 2004/0176703 A1 | 9/2004 | Christensen et al. | |
| 2004/0193328 A1 | 9/2004 | Zaitsu et al. | |
| 2004/0243075 A1 | 12/2004 | Harvie | |
| 2005/0027254 A1 | 2/2005 | Vasko | |
| 2005/0065464 A1 | 3/2005 | Talbot et al. | |
| 2005/0085760 A1 | 4/2005 | Ware et al. | |
| 2006/0052764 A1 | 3/2006 | Gelfand et al. | |
| 2006/0064053 A1 | 3/2006 | Bollish et al. | |
| 2006/0100743 A1 | 5/2006 | Townsend et al. | |
| 2006/0184084 A1 | 8/2006 | Ware et al. | |
| 2006/0235353 A1 | 10/2006 | Gelfand et al. | |
| 2006/0253064 A1 | 11/2006 | Gelfand et al. | |
| 2006/0270971 A1 | 11/2006 | Gelfand et al. | |
| 2007/0055198 A1 | 3/2007 | O'Mahony et al. | |
| 2007/0088333 A1 | 4/2007 | Levin et al. | |
| 2008/0027409 A1 | 1/2008 | Rudko et al. | |
| 2008/0033394 A1 | 2/2008 | Gelfand et al. | |
| 2008/0051764 A1 | 2/2008 | Dent et al. | |
| 2008/0171966 A1 | 7/2008 | Rudko et al. | |
| 2008/0221512 A1 | 9/2008 | Da Silva et al. | |
| 2009/0054745 A1 | 2/2009 | Jennewine | |
| 2009/0062730 A1 | 3/2009 | Woo | |
| 2010/0133510 A1 | 6/2010 | Kim et al. | |
| 2010/0185175 A1 | 7/2010 | Kamen | |
| 2010/0280443 A1 | 11/2010 | Gelfand et al. | |
| 2010/0280444 A1 | 11/2010 | Gelfand et al. | |
| 2010/0286559 A1 | 11/2010 | Paz et al. | |
| 2010/0312039 A1 | 12/2010 | Quirico | |
| 2011/0046514 A1 | 2/2011 | Greenwald et al. | |
| 2011/0046516 A1 | 2/2011 | Paz et al. | |
| 2011/0120231 A1 | 5/2011 | Berger | |
| 2011/0196304 A1 | 8/2011 | Kramer et al. | |
| 2011/0218411 A1 | 9/2011 | Keenan | |
| 2011/0288524 A1 | 11/2011 | Gelfand et al. | |
| 2012/0078137 A1 | 3/2012 | Mendels | |
| 2012/0259308 A1 | 10/2012 | Gelfand | |
| 2013/0104667 A1 | 5/2013 | Koyano | |
| 2013/0235691 A1 | 9/2013 | Volker | |
| 2013/0261412 A1 | 10/2013 | Reed | |
| 2013/0274705 A1 | 10/2013 | Burnes et al. | |
| 2014/0031787 A1 | 1/2014 | Burnes et al. | |
| 2014/0073973 A1 | 3/2014 | Sexton | |
| 2014/0228755 A1 | 8/2014 | Darrah et al. | |
| 2014/0260600 A1 | 9/2014 | Rike | |
| 2014/0366641 A1 | 12/2014 | Jedema et al. | |
| 2015/0105694 A1 | 4/2015 | Mahajan | |
| 2015/0233749 A1 | 8/2015 | Wang et al. | |
| 2015/0258277 A1 | 9/2015 | Halpert | |
| 2016/0051176 A1 | 2/2016 | Ramos et al. | |
| 2016/0051750 A1 | 2/2016 | Tsoukalis | |
| 2016/0136356 A1* | 5/2016 | Ribble ............... A61B 5/14552 705/2 |
| 2017/0016755 A1 | 1/2017 | Boussange et al. | |
| 2017/0052056 A1 | 2/2017 | Yamasaki et al. | |

(56) References Cited

U.S. PATENT DOCUMENTS

| | | | |
|---|---|---|---|
| 2017/0290974 A1 | 10/2017 | Tsoukalis | |
| 2018/0071455 A9 | 3/2018 | Halpert | |
| 2018/0110455 A1 | 4/2018 | Chang et al. | |
| 2018/0177945 A1 | 6/2018 | Sims et al. | |
| 2018/0245967 A1 | 8/2018 | Parker et al. | |
| 2018/0250461 A1* | 9/2018 | Gura ................... | A61M 1/3679 |
| 2018/0280620 A1 | 10/2018 | Reichthalhammer | |
| 2019/0001057 A1 | 1/2019 | Tsoukalis | |
| 2019/0038833 A1 | 2/2019 | Pirazzoli et al. | |
| 2019/0262532 A1 | 8/2019 | Oh et al. | |
| 2019/0321588 A1 | 10/2019 | Burnett | |
| 2020/0230351 A1 | 7/2020 | Kelly et al. | |
| 2020/0284234 A1 | 9/2020 | Huberts et al. | |
| 2020/0324044 A1 | 10/2020 | Gylland et al. | |
| 2020/0360604 A1 | 11/2020 | Kolko et al. | |
| 2020/0405955 A1 | 12/2020 | Shah et al. | |
| 2021/0024536 A1 | 1/2021 | Bhattacharya | |
| 2021/0077007 A1 | 3/2021 | Jouret et al. | |
| 2021/0085853 A1 | 3/2021 | Chen et al. | |
| 2021/0128815 A1 | 5/2021 | Byrne et al. | |
| 2021/0162188 A1 | 6/2021 | Cui | |
| 2021/0169408 A1 | 6/2021 | Levin | |
| 2021/0170084 A1 | 6/2021 | Zacharia | |
| 2021/0196880 A1 | 7/2021 | O'Mahony et al. | |
| 2021/0236727 A1 | 8/2021 | Levin et al. | |
| 2021/0244381 A1 | 8/2021 | Sweeney et al. | |
| 2021/0260306 A1 | 8/2021 | Gravenstein et al. | |
| 2021/0283357 A1 | 9/2021 | Leonard | |
| 2021/0298653 A1 | 9/2021 | Woodward et al. | |
| 2021/0369959 A1 | 12/2021 | Abal et al. | |
| 2022/0152302 A1 | 5/2022 | Halpert | |
| 2022/0273213 A1 | 9/2022 | Sokolov | |
| 2022/0288362 A1 | 9/2022 | Porter et al. | |
| 2022/0296140 A1 | 9/2022 | Nguyen | |
| 2022/0296406 A1 | 9/2022 | Keelen | |
| 2022/0313158 A1 | 10/2022 | Levin et al. | |
| 2022/0330866 A1 | 10/2022 | Conley et al. | |
| 2022/0330867 A1 | 10/2022 | Conley et al. | |
| 2022/0339622 A1 | 10/2022 | Conley et al. | |
| 2023/0010793 A1 | 1/2023 | Testani | |
| 2023/0068431 A1 | 3/2023 | Erbey et al. | |
| 2023/0414871 A1 | 12/2023 | Halpert | |
| 2024/0347162 A1 | 10/2024 | Meese | |

FOREIGN PATENT DOCUMENTS

| | | |
|---|---|---|
| EP | 3278833 | 2/2018 |
| EP | 4108171 | 12/2022 |
| GB | 2560580 A | 9/2018 |
| JP | 2008110150 | 5/2008 |
| JP | 2010503515 | 2/2010 |
| JP | A-2011-520549 | 7/2011 |
| JP | A-2017-536857 | 2/2017 |
| KR | 10-2022-0035738 | 3/2022 |
| WO | WO-1996016685 | 6/1996 |
| WO | WO-1996028209 | 9/1996 |
| WO | WO-1997016220 | 5/1997 |
| WO | WO-1999006087 | 2/1999 |
| WO | WO-2005102441 | 11/2005 |
| WO | WO-2006041496 | 4/2006 |
| WO | WO-2009029899 | 3/2009 |
| WO | WO-2013154783 | 10/2013 |
| WO | 2014022422 A1 | 2/2014 |
| WO | WO-2015142617 | 9/2015 |
| WO | 2016103256 A1 | 6/2016 |
| WO | 2018114794 A1 | 6/2018 |
| WO | WO-2019222485 | 11/2019 |
| WO | WO-2020033752 | 2/2020 |
| WO | 2021205345 | 10/2021 |
| WO | WO-2022219578 | 10/2022 |
| WO | 2022259115 | 12/2022 |
| WO | 2024013731 | 1/2024 |

OTHER PUBLICATIONS

U.S. Appl. No. 18/434,540, filed Feb. 6, 2024, Halpert.

U.S. Appl. No. 18/595,182, filed Mar. 4, 2024, Levin.

U.S. Appl. No. 18/637,340, filed Apr. 16, 2024, Conley et al.

U.S. Appl. No. 18/641,241, filed Apr. 19, 2024, Da Silva.

"2016 ESC Guidelines for the Diagnosis and Treatment of Acute and Chronic Heart Failure—Web Addenda," European Heart Journal, 17 pages.

Abraham Otero, "A New Device to Automate the Monitoring of Critical Patients' Urine Output", Hindawi Publishing Corp, BioMed Research Int'l, vol. 2014, Article ID 587593, 8 pages.

Adams et al., "Executive Summary: HFSA 2006 Comprehensive Heart Failure Practice Guideline," Journal of Cardiac Failure, vol. 12, No. 1, 2006, pp. 10-38.

Adaptec Medical Devices, "Ongoing Access to Real-Time and Accurate Monitoring of Urine Output Could Improve Management of Critically Ill Patients," Clinical Literature Review, (2016) 8 pages.

Alison Shepherd, "Measuring and Managing Fluid Balance", Nursing Times, vol. 107, No. 28, pp. 12-16 (Jul. 19, 2011) 5 pages.

Allen et al., "Continuous Versus Bolus Dosing of Furosemide for Patients Hospitalized for Heart Failure," American Journal of Cardiology, 105(12): 1794-1794, 2010.

Antonio Tricoli, "Miniaturized Bio-and Chemical-Sensors for Point-of-Care Monitoring of Chronic Kidney Diseases," Sensors 2018, 18, 942; (Mar. 22, 2018) 18 pages.

Baliga, "Diuretic Therapy for Heart Failure Patients," American College of Cardiology, 75:1178- 1195, 2020.

Barbara Lara, "Accurate Monitoring of Intravascular Fluid Volume: A Novel Application of Intrathoracic Impedance Measures for the Guidance of Volume Reduction Therapy," IJC Heart & Vasculature, 8 (2015) pp. 47-51, 5pages.

Bell et al., "Risk of Postoperative Acute Kidney Injury in Patients Undergoing Orthopaedic Surgery—Development and Validation of Risk score and Effect of Acute Kidney Injury on Survival: Observational Cohort Study," BMJ: 2015, 9 pages.

Bouman et al., "Red Blood Cell Transfusion and Furosemide in Cardiac Surgery: Friend and Foe?" The Netherlands Journal of Medicine, Dec. 2012, vol. 70, No. 10, 3 pages.

Brater, "Diuretic Therapy," New England Journal of Medicine, 339:387-395, 1998.

Cosgrove III et al., "Automated Control Postoperative Hypertension: A Prospective Randomized Multicenter Study," 1989 by The Society of Thoracic Surgeons, 6 pages.

David Farcy, "Review: Pitfalls in Using Central Venous Pressure as a Marker of Fluid Responsiveness," Emergency Medicine. Jan. 2016;48(1):18-28, 15 pages.

Ellison et al., "Diuretic Treatment in Heart Failure," New England Journal of Medicine, 377:1964-1975, 2017.

Farkas, "Deresuscitation: Dominating the Diuresis," The Internet Book of Critical Care, 43 pages, 2020.

Furutani et al., "An Automatic Control System of the Blood Pressure of Patients Under Surgical Operation," International Journal of Control, Automation, and Systems, vol. 2, No. 1, Mar. 2004, pp. 39-54.

Gheorghiade et al., "Current Medical Therapy for Advanced Heart Failure," American Heart Journal, Jun. 1998, pp. S231-S248.

Goren et al., "Perioperative Acute Kidney Injury," British Journal of Anaesthesia, 2015, 12 pages.

Hasselblad et al., "Relation Between Dose of Loop Diuretics and Outcomes in a Heart Failure Population: Results of the ESCAPE Trial", European Journal of Heart Failure, 9(10):1064-1069, 2007.

Josephs et al., "Perioperative Risk Assessment, Prevention, and Treatment of Acute Kidney Injury," International Anesthesiology Clinics, vol. 47, No. 4, www.anesthesiaclinics.com, pp. 89-105.

Kambiz Kalantari, "Assessment of Intravascular Volume Status and Volume Responsiveness in Critically Ill Patients," Kidney International (2013) 83, 1017-1028 (Jan. 9, 2013) 12 pages.

Kolh, "Renal Insufficiency After Cardiac Surgery: A Challenging Clinical Problem," European Heart Journal, 2009, pp. 1824-1827.

Kui Jin et al., "Intensive Monitoring of Urine Output Is Associated With Increased Detection of Acute Kidney Injury and Improved Outcomes," Chest Journal - Original Research Critical Care, 152#5, pp. 972-979 (Nov. 2017) 8 pages.

(56)                    References Cited

OTHER PUBLICATIONS

Lassnigg et al., "Lack of Renoprotective Effects of Dopamine and Furosemide During Cardiac Surgery," J. Am Soc Nephrol, 2000, pp. 97-104.

Lenihan et al., "Trends in Acute Kidney Injury, Associated Use of Dialysis and Mortality After Cardiac Surgery, 1999 to 2008," Ann Thorac Surg. 2013, 17 pages.

Marenzi et al., "Prevention of Contrast Nephropathy by Furosemide With Matched Hydration," JACC: Cardiovascular Interventions, 5(1):90-97, 2011.

Mayo Clinic, "Creatinine Test", Mayo Foundation for Medical Education and Research (MFMER) (downloaded Aug. 16, 2018).

Meersch et al., "Perioperative Acute Kidney Injury: An Under-Recognized Problem," vol. 125, No. 4, www.anesthesia-analgesia.org, Oct. 2017, pp. 1223-1232.

Mendeley et al., "Furosemide", Science Direct, 5 pages, 2016.

Oh et al., "Loop Diuretics in Clinical Practice," Review: Electrolyte Blood Press, 13(1): 5 pages, 2015.

Olivero et al., "Acute Kidney Injury After Cardiovascular Surgery: An Overview," debakeyheartcenter.com/journal, 2012, pp. 31-36.

Palazzuli et al. "Continuous versus bolus intermittent loop diuretic infusion in acutely decompensated heart failure: a prospective randomized trial," Critical Care 18, 2014.

Prandota et al., "Pharmacokinetics and metabolism of furosemide in man," European Journal of Drug Metabolism and Pharmcokinetics, 1(4): 5 pages, 1976.

Rosenberg et al., "Combination Therapy with Metolazone and Loop Diuretics in Outpatients with Refactory Heart Failure: An Observational Study and Review of the Literature," Cardiovascular Drugs and Therapy, Kluwer Academic Publishers, vol. 19, No. 4, Aug. 2005, 6 pages.

Rui Geng et al., "Identification of Modifiable Risk Factors for Acute Kidney Injury After Coronary Artery Bypass Graft Surgery in an Asian Population," The Journal of Thoracic and Cardiovascular Surgery, Apr. 2014, pp. 1356-1361.

Se Won Oh et al., "Loop Diuretics in Clinical Practice", Electrolytes & Blood Pressure, www.ncbi.nlm.nih.gov/pmc/articles/PMC4520883, printed Mar. 25, 2019, 6 pages.

Sheldon Magder et al., "The Clinical Role of Central Venous Pressure Measurements", Journal of Intensive Care Medicine 22(1); 207, 8 pages.

Stickler et al., "A Sensor to Detect the Early Stages in the Development of Crystalline Proteus mirabilis Biofilm on Indwelling Bladder Catheters", Journal of Clinical Microbiology, Apr. 2006, p. 1540-1542.

Teixeira et al., "Fluid Balance and Urine Volume are Independent Predictors of Mortality in Acute Kidney Injury", Critical Care 17:R14 (2013) 11 pages.

Testani et al., "Rapid and Highly Accurate Prediction of Poor Loop Diuretic Natriuretic Response in Patients with Heart Failure," Circulation; Heart Failure, vol. 9. No. 1, 2016, 32 pages.

Thakar, "Perioperative Acute Kidney Injury," Advances in Chronic Kidney Disease, vol. 20, No. 1, 2013, pp. 67-75.

Unknown Author, "Furosemide Drug Summary," Prescriber's Digital Reference, pp. 1-31, 2016.

Vellinga et al., "Identification of Modifiable Risk Factors for Acute Kidney Injury After Cardiac Surgery," The Netherlands Journal of Medicine, vol. 70, No. 10, Dec. 2012, pp. 450-454.

Vivane Conradds, "Sensitivity and Positive Predictive Value of Implantable Intrathoracic Impedance Monitoring as a Predictor of Heart Failure Hospitalizations: The SENSE-HF Trial," European Heart Journal (2011) 32, 2266-2273, 8pages.

Yeh et al., "Goal-directed diuresis: A case—control study of continuous furosemide infusion in critically ill trauma patients", The Journal of Emergencies, Trauma, and Shock, 8(1): 34-38, 2015.

Written Opinion of the International Searching Authority for PCT Application No. PCT/US2005/008948 dated Oct. 3, 2006, 3 pages.

Written Opinion of the International Searching Authority for PCT Application No. PCT/US2007/021791 dated May 8, 2008, 7 pages.

Written Opinion of the International Searching Authority for PCT Application No. PCT/U20S07/009685 dated Jul. 18, 2008, 10 pages.

Written Opinion of the International Searching Authority for PCT Application No. PCT/US2007/009684 dated Jul. 21, 2008, 7 pages.

Written Opinion of the International Searching Authority for PCT Application No. PCT/US2008/007845 dated Sep. 17, 2008, 5 pages.

Written Opinion of the International Searching Authority for PCT Application No. PCT/US2008/007841 dated Sep. 18, 2008 4 pages.

Written Opinion of the International Searching Authority for PCT Application No. PCT/US2007/009683 dated Nov. 24, 2008, 6 pages.

Written Opinion of the International Searching Authority for PCT Application No. PCT/US2009/002739 dated Jun. 19, 2009, 4 pages.

Written Opinion of the International Searching Authority for PCT Application No. PCT/US2010/000137 dated Mar. 16, 2010, 8 pages.

Written Opinion of the International Searching Authority for PCT Application No. PCT/US2015/020196, dated Jun. 12, 2015, 5 pages.

Bart et al., "Ultrafiltration in Decompensated Heart Failure With Cardiorenal Syndrome", The New England Journal of Medicine, Dec. 13, 2012, 9 pages, Massachusetts Medical Society.

Brezis et al., Hypoxia of the Renal Medulla—Its Implications for Disease, New England Journal of Medicine, vol. 322, No. 10, Mar. 9, 1995, 9 pages.

Briguori et al., "Renal Insufficiency After Contrast Media Administration Trial II (Remedial II): RenalGuard System in High-Risk Patients for Contrast-Induced Acute Kidney Injury", Circulation, Journal of the American Heart Association, Mar. 13, 2011, 10 pages.

Dorval et al., "Feasibility Study of the RenalGuard™ Balanced Hydration System: A Novel Strategy for the Prevention of Contrast-Induced Nephropathy in High Risk Patients", International Journal of Cardiology, 2011, 5 pages, Elsevier Ireland Ltd.

Edelson et al., Pharmacokinetics of Iohexol, a New Nonionic Radiocontrast Agent, in Humans, Journal of Pharmaceutical Sciences, vol. 73, No. 7, Jul. 1984, 3 pages.

Felker et al., "Diuretic Strategies in Patients With Acute Decompensated Heart Failure", The New England Journal of Medicine, Mar. 3, 2011, vol. 364, No. 9, 9 pages.

Gloor, James M. and Vincente E. Torres, Reflux and Obstructive Nephropathy, Atlas of Diseases of the Kidney, on-line edition, vol. Two, Section I, Ch. 8, pp. 8.1-8.25, 1999, 27 pages.

Hvistendahl et al., Renal Hemodynamic Response to Gradated Ureter Obstruction in the Pig, Nephron 1996, 74:168-74, 7 pages.

Lelarge et al., Acute Unilateral Renal Failure and Contralateral Ureteral Obstruction, American Journal of Kidney Diseases, vol. XX, No. 3, Sep. 1992, 3 pages.

Levin et al. High-volume diuresis with matched maintenance of intravascular volume may prevent contrast-induced nephropathy in post-transplant patients with moderate-severe baseline renal impairment, Cardiovascular Revascularization Medicine, Elsevier, NL, vol. 8, No. 2, Apr. 1, 2007, 1 page.

Lloyd-Jones et al., "Heart Disease and Stroke Statistics—2009 Update. A Report From the American Heart Association Statistics Committee and Stroke Statistics Subcommittee", Circulation, Journal of the American Heart Association, Jan. 27, 2009, 161 pages.

Marenzi et al.. "Prevention of Contrast Nephropathy by Furosemide With matched Hydration. The MYTHOS (Induced Diuresis With Matched Hydration Compared to Standard Hydration for Contrast Induced Nephropathy Prevention) Trial", JACC: Cardiovascular Interventions, vol. 5, No. 1, 2012 The American College of Cardiology Foundation, 8 pages.

Mawer et al., "Value of Forced Diuresis in Acute Barbiturate Poisoning", Jun. 29, 1968, British Medical Journal, 2, 4 pages.

Paterna et al., "Changes in Brain Natriuretic Peptide Levels and Bioelectrical Impedance Measurements After Treatment With High-Dose Furosemide and Hypertonic Saline Solution Versus High-Dose Furosemide Alone in Refractory Congestive Heart Failure", Journal of the American College of Cardiology, 2005, vol. 45, No. 12, 7 pages.

(56)          References Cited

OTHER PUBLICATIONS

Pederson et al., Renal Water and Sodium Handling During Gradated Unilateral Ureter Obstruction, Scand J. Urol Nephrol, 2002, 36:163-72, 11 pages.

Rihal et al., Incidence and Prognostic Importance of Acute Renal Failure After Percutaneous Coronary Intervention, Circulation, May 14, 2002, 6 pages.

Rosamilia et al., Electromotive Drug Administration of Lidocaine and Dexamethasone Followed by Cystodistension in Women with Interstitial Cystitis, International Urogyecologyl Journal, Pelvic Floor Dysfunction 1997; 8: 142-5, 4 pages.

S215 Ultra Low Profile Single Point Load Cell-Strain Guage Sensors and Load Cells, Ultra-Low Profile Single Point Load Cell—S215, http://smdsensors.com/detail_pgs/s215.htm 2005, 3 pages.

Solomon et al., Effects of Saline, Mannitol, and Furosemide on Acute Decreases in Renal Function Induced by Radiocontrast Agents, The New England Journal of Medicine, vol. 331: 1416-1420, Nov. 24, 1994, No. 21, 5 pages.

Stevens, Melissa A., MD et al., A Prospective Randomized Trial of Prevention Measures in Patients at High Risk for Contrast Nephropathy, Results of the P.R.I.N.C.E. Study, Journal of American College of Cardiology, vol. 33, No. 2, Feb. 1999, 9 pages.

Stevenson et al., "Editorial Comment, Torrent or Torment From the Tubules?", Challenge of the Cardiorenal Connections, Journal of the American College of Cardiology, vol. 45, No. 12, 2005, 4 pages.

Wakelkamp et al., The influence of drug input rate on the development of tolerance to frusemide, Br. J. Clin. Pharmacol 1998, 46:479-487, 9 pages.

Weinstein et al., Potential deleterious Effect of Furosmide in Radiocontrast Nephropathy, Department of Medicine, Hadassah Univeristy Hospital, Mount Scopus, Jerusalem, Israel, Nephron 1992, 62: 413-415, pages.

Doty et al., Effect of Increased Renal Venous Pressure on Renal Function, The Journal of Trauma: Injury, Infection and Critical Care, vol. 47, No. 6, Dec. 1999, 4 pages.

Heyman et al., Pathophysiology of Radiocontrast Nephropathy: A Role for Medullary Hypoxia, Investigative Radiology, vol. 34, No. 11, Nov. 1999, 7 pages.

Phillips et al., "Measurement of sodium Ion concentration in undiluted urine with cation-selective polymeric membrane electrodes after the removal of interfering compounds", Talanta, Elsevier, Amsterdam, NL, vol. 74, No. 2, Nov. 15, 2007, pp. 255-264.

International Search Report and Written Opinion mailed Jul. 8, 2022; International Patent Application No. PCT/US2022/071932; 17 pages.

Felker et al., "Diuretic Therapy for Heart Failure Patients," American College of Cardiology, Mar. 9, 2020, 4 pages.

* cited by examiner

1

MEASURING AND/OR DETECTING ANALYTES IN URINE, AND ASSOCIATED SYSTEMS, DEVICES, AND METHODS

CROSS-REFERENCE TO RELATED APPLICATIONS

The present application is related to U.S. application Ser. No. 17/659,393, filed Apr. 15, 2022, and claims priority to U.S. Prov. Pat. App. No. 63/179,975, filed Apr. 26, 2021, and U.S. Prov. Pat. App. No. 63/203,818, filed Jul. 30, 2021, the disclosures of which are each incorporated herein by reference in their entireties.

TECHNICAL FIELD

The present technology relates to measuring and/or detecting the concentrations and other characteristics of analytes in urine, and associated systems, devices, and methods.

BACKGROUND

Human physiological systems seek to naturally maintain a balance between fluid intake and fluid excretion. An imbalance in fluid intake and excretion rates may cause the body to retain excess amounts of fluid, also known as fluid overload. Fluid overload can be caused by acute decompensated heart failure (ADHF), chronic heart failure (CHF), or other conditions in which insufficient fluid is excreted. Patients exhibiting fluid overload may suffer from shortness of breath (dyspnea), edema, hypertension, and other undesirable medical conditions.

To treat fluid overload, patients are typically administered a diuretic drug which induces and/or increases urine production, thus reducing the amount of fluid and sodium in the body. The rate of urine output may be carefully monitored and/or controlled for safety reasons, e.g., to avoid placing undue stress on the patient's kidneys. Different patients may respond differently to treatment, such that the same diuretic type and/or dosage may produce drastically different urine output rates. However, conventional systems and methods for treating fluid overload may not be capable of accurately monitoring a patient's urine output and/or responding to changes in urine output.

DETAILED DESCRIPTION

Figure 1:
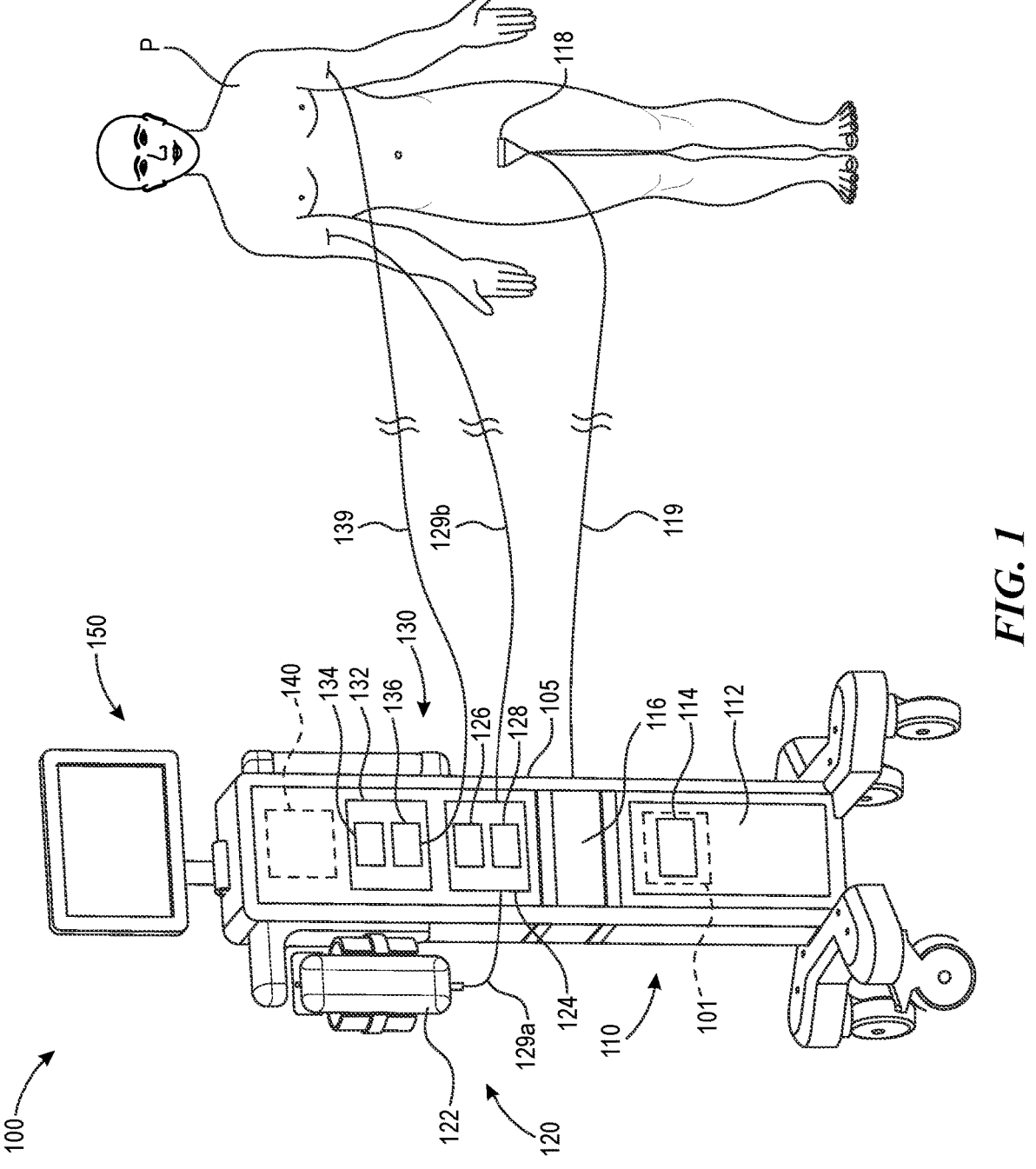
FIG. 1 is a partially schematic illustration of a fluid management system for monitoring urine output and/or control fluid infusion into a patient, in accordance with embodiments of the present technology.

In some embodiments, the systems, devices, and methods described herein are used to treat a patient for fluid overload. To treat fluid overload, patients can be administered a diuretic drug which induces and/or increases urine production. For example, loop diuretics are diuretics that act at the ascending limb of the loop of Henle in the kidney, and include bumetanide (Bumex®), ethacrynic acid (Edecrin®), furosemide (Lasix®), torsemide (Demadex®), thiazide diuretics (e.g., chlorothiazide, metolazone), potassium-sparing diuretics (e.g., amiloride, spironolactone), carbonic anhydrase inhibitors (e.g., acetazolamide), and osmotic diuretics (e.g., mannitol). Diuretics can be given orally as a pill or as an intravenous (IV) injection. IV diuretics can be used when oral diuretics are no longer effective and/or able to be absorbed.

The short-term effects of diuretics on a patient's urine production may be difficult to predict, particularly at early stages of treatment. For example, one patient may produce much less urine than expected for a given dose of diuretic, while another patient administered the same dose may produce very large amounts of urine. Low urine production can prolong treatment time and/or reduce treatment efficacy, while high urine production can raise concerns of hypotension, hypovolemia, electrolyte imbalance (e.g., hypokalemia), and/or vital organ damage. High doses of a diuretic, regardless of the urine response, can also raise concerns about ototoxicity. Due to these uncertainties, physicians typically initially prescribe a conservative (e.g., low) diuretic dosage and wait a few hours before considering whether to increase the dosage. If the physician determines that a higher diuretic dosage is needed, the physician may slowly and incrementally increase the dosage until the patient's urine output reaches the desired level and/or rate. However, this approach can prolong the time the patient remains in the fluid overloaded condition, which can exacerbate the patient's underlying clinical state. For example, conservative treatment procedures can require hours or even days before the patient's urine output is sufficiently high to cause significant fluid loss and relieve the fluid overload condition. The patient may be hospitalized for several days (e.g., 4-5 days), which can be expensive and burdensome. Additionally, the long-term treatment efficacy may be limited, such that approximately 25% of patients are readmitted for fluid overload within 30 days.

The present technology can address these and other challenges by providing rapid and/or accurate measurements of various analytes in the patient's urine, which can inform the therapy administered to the patient (e.g., diuretic dosage rate, hydration fluid infusion rate, etc.). Accordingly, embodiments of the present technology can (i) improve efficacy, safety, and quality of fluid management treatment, (ii) improve resource management in hospitals and other clinical settings, (iii) quickly assess if a patient is diuretic resistant, and/or (iv) increase diuretic efficiency (the amount of urine and/or excreted electrolytes (e.g., sodium) obtained over a given time per mg of diuretic infused intravenously). Moreover, the embodiments described herein can increase net removal of fluid and/or electrolytes (e.g., sodium and/or chloride), and can also treat fluid overload conditions in a more efficient manner (e.g., shorter timeframe and/or higher net fluid loss).

In some embodiments, a fluid therapy system configured in accordance with embodiments of the present technology includes a urine analysis cartridge fluidly coupled to a patient and configured to receive urine therefrom. The urine analysis cartridge can include a urine inlet configured to receive urine from a patient, a urine outlet, a flow channel extending between the urine inlet and urine outlet, and sensors fluidly coupled to the channel. The channel can include sensing zones, and individual sensing zones can be aligned with a corresponding one of the sensors. Each sensor is configured to generate data associated with one or more electrical (e.g., conductivity), chemical (e.g., sodium, potassium, chloride, lithium electrolyte, pH, ammonia, urea, glucose, lactate, creatine, specific gravity, and/or oxygen tension), and/or physical (e.g., temperature) properties of the urine flowing therethrough. Based at least in part on the sensor data, the fluid therapy system can control aspects of the fluid therapy provided to the patient, such as increasing or decreasing an amount or delivery rate of hydration fluid and/or diuretic. Accordingly, the sensor data generated by the cartridge can enable the fluid therapy system to more efficiently treat the patient's fluid overload condition. Additionally or alternatively, the sensors can be configured to monitor (e.g., in real-time) one or more diuretics, contrast agents, and/or other drugs infused into the patient and expelled in the urine, such that the cartridge can be used to monitor the patient's fluid management therapy, provide more accurate dosing, and/or reduce or prevent the likelihood of over- and/or under-dosing (e.g., via diuretics and/or saline).

In some embodiments, the urine analysis cartridge includes a flow control device configured to control the flow of urine thought the cartridge. The flow control device can be transitionable between (i) a first configuration in which the flow control device at least partially prevents urine flow into one of the sensing zones, and (ii) a second configuration in which the flow control device allows urine flow into one or more of the sensing zones. In some embodiments, the flow control device can be positioned between individual sensors and/or sensing zones to fluidly isolate the sensors and/or sensing zones from the urine when the flow control device is in the first configuration. Additionally or alternatively, the cartridge can include multiple flow channels arranged in parallel to one another, such that the sensors and/or sensing zones associated with one of the flow channels are fluidly isolated from the sensors and/or sensing zones associated with a different one of the flow channels. In some embodiments, fluidly isolating individual sensors and/or sensing zones can reduce or eliminate error and/or noise in the sensor data associated with "cross-communication" and/or other interference between the sensors.

Advantageously, the cartridges configured in accordance with embodiments of the present technology can provide simple, fast and/or robust measurements of urine samples at the point-of-care. In some embodiments, the cartridges are integrated devices configured to cool, transport, prepare, and/or analyze the urine samples with little or no user input or handling, which can reduce or eliminate potential sources of error associated with manual handling and/or preparation of the urine samples. In some embodiments, the cartridges can measure the patient's urine output without adding liquid reagents, which may reduce or eliminate dilution errors, extend the shelf life of the urine analysis cartridge, make the cartridge easier to use, and/or make the urine analysis cartridge more economical to manufacture. In addition, because the sensors of the cartridge are configured to measure the patient's urine output and/or properties thereof based on urine flow through the cartridge, the costs associated with sample preparation for other analytical transduction techniques (e.g., optical analysis) can be reduced or eliminated.

The headings provided herein are for convenience only and are not intended to limit or interpret the scope or meaning of the technology.

I. Fluid Management Systems and Methods

FIG. 1 is a partially schematic illustration of a fluid management system 100 ("system 100") for monitoring urine output and/or controlling fluid infusion into a patient P, in accordance with embodiments of the present technology. The system 100 includes a urine collection and monitoring system 110 ("urine system 110"), an automated hydration fluid infusion system 120 ("hydration system 120"), an automated diuretic infusion system 130 ("diuretic system 130"), a controller or control system 140 ("controller 140"), and a display or input/output unit 150 ("display 150"). The controller 140 can be operably coupled to each of the urine system 110, hydration system 120, diuretic system 130, and/or display 150. The system 100 can further include a console or structure 105 ("console 105") that incorporates, houses, and/or otherwise supports all or portions of the urine system 110, hydration system 120, diuretic system 130, the controller 140, and/or the display 150.

The urine system 110 is configured to collect urine from the patient P and/or monitor the patient's urine output (e.g., urine output amount and/or rates). The urine system 110 can include one or more collection containers 112 ("container 112") configured to hold urine, such as a disposable bag or other collection device. The container 112 can be fluidly coupled to the patient P via a fluid line 119 (e.g., a tubing line). The fluid line 119 can be connectable to a disposable catheter 118 (e.g., a Foley catheter, Texan Condom catheter, PureWick catheter, etc.) placed in or otherwise connected to the bladder of the patient P.

In some embodiments, urine flow through the fluid line 119 is driven by the patient's urine production, gravity (e.g., the bladder of the patient P is positioned higher than the container 112), and/or a siphon effect between the patient's bladder and the container 112. In other embodiments, the urine system 110 can also include a pump (not shown) operably coupled to the fluid line 119 for actuating urine flow through the fluid line 119 and into the container 112. The pump can be or include any device suitable for pumping fluid, such as a peristaltic pump. The pump can be used to initiate urine flow from the patient's body at the start of the procedure. The pump can also maintain urine flow during the treatment procedure at a desired flow rate, and can operate continuously, periodically (e.g., at predetermined time intervals), and/or in response to user input and/or detected issues (e.g., unexpected interruptions in urine flow). The pump can also be used to clear air locks and/or other obstructions from the fluid line 119. Additional examples of devices suitable for priming the fluid line 119 with fluid, pumping urine through the fluid line 119, and/or clearing air locks from the fluid line 119 can be found in U.S. application Ser. No. 17/659,393, filed Apr. 15, 2022, the disclosure of which was previously incorporated by reference herein.

The urine system 110 can include one or more sensors 114 ("sensor(s) 114") configured to detect properties of the patient's urine output (e.g., an amount and/or rate of the urine output, and/or electrical, chemical, and/or physical properties of the urine output). The sensor(s) 114 can be operably coupled to the controller 140 so the controller 140 can monitor and/or compute the patient's urine output based on the data generated by the sensor(s) 114. In some embodiments, the sensor(s) 114 can be fluidly coupled to the fluid line 119. As described in detail below (e.g., with reference to FIGS. 2A-5), the sensor(s) 114 can be integrated into a urine flow analysis cartridge 101 ("cartridge 101") configured to receive urine from the patient P. The cartridge 101 can include a flow channel fluidly coupled to the fluid line 119, and the sensor(s) 114 can be positioned within the flow channel. Accordingly, as urine flows through the cartridge 101, the sensor(s) 114 can generate data based at least partially on the patient's urine such that the controller 140 can monitor and/or compute the patient's urine output. In some embodiments, the fluid line 119 can be coupled directed to the cartridge 101, for example, to a fluid inlet of the cartridge 101. Additionally or alternatively, the cartridge 101 can be integrated with the console 105, detachably coupled to the console 105, integrated into the fluid line 119, and/or have another suitable configuration relative to one or more other components of the system 100.

The urine output can be determined in many different ways, such as based on urine flow (e.g., through the fluid line 119, the cartridge 101, and/or into the container 112), the amount of urine in the container 112 (e.g., based on the weight of the container 112, level of urine in the container 112, etc.), and/or other properties associated with the urine. The sensor(s) 114 can include one or more of the following: a flow sensor, drip counter, fluid weight sensor, fluid level sensor, float sensor, optical sensor, ultrasonic sensor, contact-based sensor (e.g., a paddle wheel sensor), and/or the sensors described in detail below with reference to FIGS. 2A-5. As shown in FIG. 1, the sensor(s) 114 are positioned at the console 105. In other embodiments, however, some or all of the sensor(s) 114 can be at a different location in the system 100, such as on or in the line 119, the container 112, and/or the patient P.

In some embodiments, the sensor(s) 114 can include at least one sensor configured to measure one or more characteristics of the urine, in addition to detecting the patient's urine output. For example, the sensor(s) 114 can be configured to measure urine temperature, urine conductivity, urine oxygenation, urine specific gravity, levels of one or more analytes in the urine (e.g., sodium ions, potassium ions, chloride ions, lithium, electrolytes, pH, ammonia, urea, glucose, lactate, creatine, and/or hormones), and/or other urine characteristics described in detail with reference to FIGS. 2A-5. Additionally or alternatively, the sensor(s) 114 can be configured to detect and/or measure one or more diuretics, other drugs, contrast agents, and/or metabolized versions thereof that are currently being administered, that were previously administered to the patient P, and/or that were altered pre- or post-electrochemical measurements. Such characteristics can be useful, e.g., in determining effectiveness of a particular therapy and/or whether the patient P is in or could be approaching a critical condition. For example, urine conductivity and/or urine electrolytes (e.g., sodium) can indicate whether the patient is responding well to the fluid therapy, or whether the patient is in a critical condition and fluid therapy should cease. In some embodiments, urine conductivity (either alone or in combination with urine specific gravity) is used as a proxy for measurements of urine sodium and/or other urine electrolytes. For example, a higher urine conductivity can correlate to higher urine sodium levels and a lower urine conductivity can correlate to lower urine sodium levels. As another example, urine temperature measurements can be used to detect urine flow (e.g., based on heat loss through the fluid line 119 and/or the cartridge). The urine temperature can also be used as a proxy for the patient's body temperature, which in turn can correlate to the patient's current clinical state.

Optionally, the sensor(s) 114 can include at least one sensor configured to monitor the status of the urine collection procedure, such as whether urine collection is proceeding normally, whether there are interruptions in urine flow, whether there is a blockage or leak in the urine system 110 and/or the cartridge 101, etc. For example, the sensor(s) 114 can include a leak sensor configured to detect whether a leakage is present in the urine system 110 (e.g., at or near the fluid line 119, catheter 118, cartridge 101, and/or container

112). Leaks can be detected based on changes in urine flow rate, changes in pressure, the presence of moisture, or any other suitable parameter. In some embodiments, the controller 140 is configured to analyze the data from the leak sensor and/or other sensor(s) 114 to differentiate between low urine output rates versus leaks in the urine system 110.

As another example, the sensor(s) 114 can include a pressure sensor configured to measure the fluid pressure in the fluid line 119. The controller 140 can use the pressure measurements to monitor the status of urine flow, and optionally, detect whether there are any interruptions (e.g., decreases, sudden stoppages) or other issues with urine collection. In some embodiments, the controller 140 analyzes the pressure measurements to determine whether interruptions are due to low urine flow (e.g., the patient's bladder is empty or nearly empty), an air lock or other obstruction in the fluid line 119, a leak in the urine system 110 and/or a kink in the fluid line 119 and/or catheter 118. The controller 140 can alert the user if manual intervention is helpful or needed (e.g., to clear the obstruction, fix the leak, remove kinks from the fluid line 119, etc.). In embodiments where the urine system 110 includes a pump, the controller 140 can automatically activate the pump and/or increase the pumping rate to clear the obstruction from the fluid line 119.

The hydration system 120 can include at least one hydration fluid source 122 ("fluid source 122"; a bag, bottle, reservoir, etc.) containing a hydration fluid, such as saline (e.g., a premixed saline solution), Ringler's lactate solution, and/or other any other liquid solution suitable for infusion in the patient P. The hydration fluid can be isotonic, hypertonic, or hypotonic, e.g., depending on the patient's condition and/or other treatment considerations. Optionally, the composition of the hydration fluid (e.g., sodium, chloride, potassium, bicarbonate, etc.) can be varied based on the patient's condition and/or expected or measured electrolyte loss during the treatment procedure.

The fluid source 122 can be connected to the patient P via at least one fluid line (e.g., an IV line or other tubing), such as first fluid line 129*a* and a second fluid line 129*b*. The fluid source 122 can be operably coupled to one or more hydration fluid components 124 for actuating and/or monitoring hydration fluid infusion via the first and second fluid lines 129*a-b*, such as a hydration fluid pump 126 and/or at least one hydration fluid sensor 128 ("fluid sensor 128"). In the illustrated embodiment, the fluid source 122 is fluidly coupled to the hydration fluid pump 126 via the first fluid line 129*a*, and the hydration fluid pump 126 can pump the hydration fluid into the patient P via the second fluid line 129*b*. The hydration fluid pump 126 can be or include a peristaltic pump or other pump suitable for infusing a fluid into the patient's body (e.g., via an IV route or another route).

The fluid sensor 128 can be configured to determine an amount and/or rate of hydration fluid flowing from the fluid source 122 toward the patient P, and can include a flow sensor, pressure sensor, and/or other sensor configured to determine fluid output from the pump 126. Alternatively or in combination, the fluid sensor 128 can monitor hydration infusion rate by measuring the pumping rate of the pump 126 (e.g., the number of rotations of the pump 126 per minute). As described elsewhere herein, the controller 140 can be operatively coupled to the hydration system 120 and can receive sensor data from the fluid sensor 128 to determine a hydration fluid infusion rate. The controller 140 can control the pumping rate of the pump 126 to control the amount and/or rate of hydration fluid provided to the patient P.

Optionally, the amount of hydration fluid in the fluid source 122 can be monitored, e.g., based on weight, volume, fluid levels, flow rates, etc. In such embodiments, the fluid source 122 can be operably coupled to an additional sensor separate from the fluid sensor 128 (not shown), such as a fluid level monitor, float sensor, weight sensor, optical sensor, drip counter, flow measurement sensor, or the like. The additional sensor can provide an independent source of measurement data for determining and/or verifying the amount and/or rate of hydration fluid being provided to the patient P, which can be helpful for improving measurement accuracy.

In some embodiments, the hydration system 120 includes at least one sensor configured to detect the presence of the fluid source 122, such as a location sensor, optical sensor, weight sensor, etc. The hydration system 120 can use the sensor data to automatically determine whether the fluid source 122 is present or absent, e.g., to assess whether the system 100 is ready to initiate the fluid therapy treatment. Optionally, the sensor data can be used to detect if the user is removing the fluid source 122 during the treatment procedure, e.g., to switch an empty or nearly empty fluid source 122 with a new fluid source 122. In such embodiments, the system 100 can automatically pause hydration fluid infusion until the fluid source 122 has been replaced. Accordingly, the user can switch fluid sources 122 without having to inform the system 100 or manually pause the procedure.

The diuretic system 130 can be configured to automatically provide a diuretic to the patient P. The diuretic system 130 can include a diuretic source 134 (e.g., syringe, bag, reservoir, etc.) containing a diuretic, such as bumetanide (Bumex®), ethacrynic acid (Edecrin®), furosemide (Lasix®), torsemide (Demadex®), and/or other diuretics known in the art, each of which may be part of a fluid solution (e.g., a mixture of saline and a diuretic or other agent). In some embodiments, the identity and/or concentration of the diuretic can be received by the controller 140 via user input (e.g., using the display 150), by scanning a barcode of the diuretic source 134 or other container of the diuretic, and/or any other suitable technique.

The diuretic source 134 can be connected to the patient P via a fluid line 139 (e.g., an IV line or other tubing). The diuretic source 134 can also be operably coupled to one or more diuretic components 136 for actuating and/or monitoring diuretic delivery via the fluid line 139. For example, the diuretic components 136 can include a diuretic pump configured to pump the diuretic through the fluid line 139 and toward the patient P. The diuretic pump can include a peristaltic pump, a syringe pump, a metering pump, or other device suitable for delivering the diuretic to the patient P at various dosage rates. The diuretic pump can deliver the diuretic according to any suitable delivery profile, such as at a controlled continuous rate and/or in controlled boluses delivered at regular intervals through the fluid line 139. Additional details of diuretic delivery profiles can be found in U.S. application Ser. No. 17/659,393, filed Apr. 15, 2022, the disclosure of which was previously incorporated by reference herein.

In some embodiments, the diuretic pump is or includes a syringe pump having a mechanical injector or plunger that is operably coupled to the controller 140, such that the controller 140 causes movement of the injector to transfer the diuretic to the patient P. The syringe pump can include or be coupled to an actuator that mechanically drives the injector to control the delivery of the diuretic to the patient P. For example, the actuator can be or include a mechanical actuator, such as a nut for rotating a screw to drive the injector. The syringe pump can also include or be operably coupled to a sensor for detecting the position of the injector. Alternatively or in combination, the diuretic pump can include other types of pumps and/or actuators. For example, the diuretic pump can include a motor, a gearbox operatively connected to the motor, a sensor for measuring rotation of said motor (e.g., a tachometer or an optical encoder), and/or a microcontroller configured to control operation of the motor and monitor the quantity of diuretic delivered to the patient P. As another example, the diuretic pump can include an electric motor, such as a rotary motor, a linear motor, and/or a series of electrically actuated solenoids configured to propel liquid from the diuretic source 134 and through the line 139 toward the patient P.

In some embodiments, the diuretic components 136 include one or more diuretic sensors configured to determine an amount and/or rate of diuretic flowing toward the patient P. The one or more diuretic sensors can include, for example, a flow sensor, weight sensor, and/or other sensor type configured to determine the amount and/or rate of diuretic delivered from the diuretic source 134. Optionally, the diuretic sensors can measure diuretic delivery based on the output from the diuretic pump, such as by monitoring the pumping rate (e.g., number of rotations of the diuretic pump per minute, plunger position, etc.). The diuretic components 136 can include additional functional components, such as an air bubble detector, pressure sensor, extravasation sensor (e.g., ivWatch device), and/or other embedded electronics, e.g., to provide feedback signals to the controller 140 to ensure accurate diuretic infusion and/or monitor infusion status.

The controller 140 is configured to automatically control hydration fluid and/or diuretic infusion (e.g., based at least in part on the patient's urine output) to promote safe and effective diuresis of the patient P. The controller 140 can include one or more processor(s) and tangible, non-transient memory configured to store programmable instructions. The controller 140 can be operably coupled to the urine system 110, hydration system 120 and/or diuretic system 130 to receive data (e.g., sensor data) from and transmit data (e.g., control signals) to the various components of these systems. For example, the controller 140 can receive sensor data from the urine system 110 (e.g., from sensor(s) 114) to determine and/or monitor the patient's urine output. Based on the urine output, the controller 140 can determine an appropriate diuretic dosage amount and/or rate to administer to the patient P, and can cause the diuretic system 130 to deliver the diuretic accordingly. For example, the controller 140 can determine a pumping rate of the diuretic pump to produce the desired delivery profile for the diuretic. Similarly, the controller 140 can determine an appropriate hydration fluid infusion rate for the patient P (e.g., based on the urine output and/or the diuretic dosage rate), and can cause the hydration system 120 to deliver the appropriate hydration fluid amount and/or rate. For example, the controller 140 can determine a pumping rate for the hydration fluid pump 126 to achieve the desired hydration fluid infusion rate. The controller 140 can regulate the diuretic dosage rate and/or hydration fluid infusion rates based on a suitable treatment regimen protocol, e.g., prescribed by a physician and/or managed by the controller 140.

During the procedure, the controller 140 can receive sensor data from the various sensors of the urine system 110, hydration system 120 and/or diuretic system 130 to monitor the urine output, hydration fluid infusion rate, and/or diuretic dosage rate, respectively. The controller 140 can also receive sensor data from additional sensors configured to monitor patient status and/or operational status of the system 100, such as fluid pressure sensors, blood pressure sensors, air bubble detectors, and the like. For example, the controller 140 can be operably coupled to at least one sensor implanted in, attached to, or otherwise associated with the patient P. The sensor(s) can provide data regarding any of the following patient parameters: pressure levels (e.g., pulmonary artery pressure, left atrial pressure), bioelectric measurements (e.g., bioimpedance vector analysis (BIVA)), hemoglobin measurements (e.g., non-invasive hemoglobin measurements), urine oxygenation levels, urine composition (e.g., creatine, sodium, potassium, chloride, etc.), urine temperature, body temperature (e.g., bladder temperature), oral fluid intake, and the like. The controller 140 can use the data from any of the sensors described herein to monitor treatment progress (e.g., whether the treatment is complete), patient status (e.g., whether the patient is responding well or poorly to treatment), and/or potential safety concerns (e.g., whether the diuresis is too aggressive, whether the patient is exhibiting side effects). The controller 140 can also adjust the hydration fluid infusion rate and/or diuretic dosage rate based on the sensor data. Additionally, the sensor data can also provide feedback to the controller 140 to confirm or verify the effectiveness of the fluid therapy.

The controller 140 can also use other data for monitoring and/or controlling the therapy, such as settings for the system 100, user input, data indicative of a desired treatment regimen (e.g., a programmed diuretic and/or hydration fluid delivery profile over time), and/or other data collected or calculated by the controller 140. In some embodiments, the data used by the controller 140 includes current and/or historical data for the patient P, such as diuretic dosages delivered to the patient P, urine output volume or rate, the amount of hydration fluid infused into the patient P, the weight or change in weight of the patient P at various times during the infusion of the diuretic, indicators of the patient's renal function (e.g., estimated glomerular Filtration Rate (eGFR)), and/or the time(s) during which the patient P was treated with the system 100.

The display 150 (e.g., a touchscreen, monitor, etc.) can include a user interface configured to receive inputs from the user and display outputs to the user. In some embodiments, the display 150 is operatively coupled to the controller 140 and thus can be used to receive user input indicating treatment parameters, such as parameters for urine output, hydration fluid infusion, and/or diuretic dosage. The treatment parameters can include, for example: a desired fluid balance level (e.g., a positive, negative, or neutral fluid balance), target fluid removal volume (e.g., minimum and/or maximum amount of fluid to be removed), desired urine output level (e.g., a total amount of urine output; a target maximum, minimum, and/or average urine output rate), treatment duration (e.g., maximum and/or minimum duration of the treatment procedure; planned duration of the input balance level and/or urine output level), hydration fluid type, hydration fluid infusion rate (e.g., maximum, minimum, and/or average infusion rate), hydration fluid infusion profile (e.g., a function indicating how the amount and/or rate of hydration fluid infusion should vary over time), time limits associated with hydration fluid infusion (e.g., maximum and/or minimum time period for hydration fluid infusion), diuretic type, diuretic dosage (e.g., maximum and/or minimum dosage), diuretic dosage rate (e.g., maximum, minimum, and/or average dosage rate), diuretic dosage profile (e.g., a function indicating how the dosage amount and/or dosage rate of diuretic should vary over time), time limits associated with diuretic delivery (e.g., maximum and/or minimum time period for diuretic delivery), other fluids received by the patient during the procedure (e.g., volume of ingested fluid, volume of fluid from other medical agents besides the diuretic and/or hydration fluid), and/or suitable combinations thereof. Other patient-related inputs may also be received at the display 150 and can include, for example, the patient's sex, weight (e.g., "dry" weight), age, ethnicity, clinical state (e.g., renal function parameters, electrolyte levels such as serum chloride levels), medical history (e.g., outcomes of previous fluid removal procedures), diagnoses (e.g., ADHF, CHF), medications (e.g., whether the patient is diuretic-naïve or diuretic-resistant), dietary factors (e.g., whether the patient is consuming a high-salt or low-salt diet, amount of oral fluid intake), etc.

Alternatively or in combination, the user input via the display 150 can prompt the controller 140 to retrieve treatment parameters (e.g., maximum diuretic dosage, maximum continuous diuretic dosage, and minimum desired urine rate) from tables and/or other data sources. The data sources can be stored in the system 100 (e.g., in a memory associated with the controller 140) and/or can be stored in a separate device (e.g., a remote computing device). In some embodiments, the controller 140 retrieves data from a remote database and/or server via a communication network (e.g., a wired network, a wireless network, a cloud-based network, the Internet, and/or suitable combinations thereof). In such embodiments, the controller 140 can be operably coupled to a communication device and/or interface configured to transmit and receive data via the communication network.

The controller 140 can output the treatment parameters to the user via the display 150 for review and/or feedback. For example, the display 150 can show recommended treatment parameters for the patient P, such as recommendations for the diuretic dosage rate (e.g., initial, maximum, and/or minimum dosage rate), hydration fluid infusion rate (e.g., initial, maximum, and/or minimum infusion rate), urine output rate (e.g., maximum and/or minimum output rate), treatment duration (e.g., maximum time period for diuretic and/or hydration fluid infusion; maximum total treatment duration), and so on. As another example, the display 150 can output one or more predetermined treatment programs so the user can select the appropriate program for the particular patient P. Optionally, the user can modify any of the displayed treatment parameters, if desired.

During the treatment procedure, the controller 140 can output information regarding procedure status to the user via the display 150. For example, the controller 140 can display information regarding any of the following: urine output (e.g., current urine output rate and/or amount, urine output rate and/or amount over time, total amount of urine output so far), hydration fluid infusion (e.g., current infusion rate and/or amount, infusion rate and/or amount over time, total amount of hydration fluid infused so far), diuretic delivery (e.g., current dosage rate and/or amount, dosage rate and/or amount over time, total amount of diuretic delivered so far), fluid balance (e.g., current fluid balance, fluid balance over time, net fluid removal so far), system status (e.g., amount of hydration fluid remaining in the fluid source 122, amount of diuretic remaining in the diuretic source 134, remaining storage capacity in the container 112), treatment time (e.g., treatment start time, projected and/or planned treatment end time, total treatment duration so far), notifications (e.g., alerts, alarms, error messages), and the like. The user can review the displayed information, and, if appropriate, provide input instructing the controller 140 to adjust, pause, and/or stop the treatment procedure.

In some embodiments, the system 100 includes redundancy in the urine system 110, hydration system 120, and/or diuretic system 130 to reduce or minimize treatment interruptions, e.g., due to running out of urine collection capacity, running out of hydration fluid, and/or running out of diuretic. For example, the system 100 can include redundant components (e.g., containers 112, fluid sources 122, and/or diuretic sources 134), which can be stored at predetermined locations (e.g., on or within the console 105 or another portion of the system 100). The controller 140 can be configured to detect the presence of the redundant components, and can automatically or semi-automatically switch between these components so the treatment procedure can continue uninterrupted or substantially uninterrupted. Alternatively or in combination, the system 100 can adjust the timing of user alerts related to urine collection capacity, hydration fluid levels, and/or diuretic levels, based on the availability of redundant components. For example, if redundant components are available, the system 100 can generate alerts at a later time (e.g., closer in time to when the container 112 would be full, when the fluid source 122 would be empty, and/or when the diuretic source 134 would be empty), since the system 100 can automatically switch to using the redundant components, or the user can rapidly perform the switch using the redundant components that are already stored locally at the system 100, rather than having to retrieve replacements from another location.

The lack of interruption in fluid therapy can help ensure effectiveness of the fluid therapy, e.g., by relieving the patient's fluid overload condition as quickly and safely as possible. In some embodiments, even brief interruptions in diuretic delivery and/or hydration fluid infusion can significantly affect the patient's urine output (e.g., cause the urine output rate to drop), which can interfere with therapeutic efficacy and prolong treatment time. The concerns described above regarding diuretic and/or hydration fluid backup supply may be unique to the present technology, e.g., due to the relatively large amounts of diuretic and/or hydration fluid that are utilized over time in some embodiments of the treatment procedures described herein. That is, whereas conventional systems and methods may utilize just a single diuretic source and/or a single hydration fluid source because of the relatively low amount of diuretic and/or hydration fluid administered, the present technology may benefit from multiple diuretic sources and/or hydration fluid sources to ensure treatment continuity. Similarly, the treatment procedures of the present technology can cause the patient P to produce relatively large volumes and/or rates of urine output compared to conventional procedures, such that multiple containers 112 may be helpful to reduce the number of times the user has to empty and/or replace the containers 112 during the procedure.

For example, in some embodiments, the urine system 110 includes two or more redundant containers 112 to ensure fluid therapy does not need to be stopped or interrupted due to the container 112 being full. In such embodiments, the urine system 110 can include a flow control assembly 116 (e.g., valves and/or other flow control components) operably coupled to the controller 140, and configured to selectively direct the urine from the patient P to one or more of the containers 112. The flow control assembly 116 can initially direct the urine received from the patient P to a first container 112. Once the flow control assembly 116 detects or determines the first container is full or nearly full (e.g., based on sensor data from the sensor(s) 114), the flow control assembly 116 can redirect the urine received from the patient P to a second container 112. While urine is being directed to the second container 112, a user can empty the first container 112 or replace the first container 112 with an empty container 112. The flow control assembly 116 and/or controller 140 can generate an alert to the user to indicate the first container is full and needs to be replaced or emptied. This process can be repeated such that fluid management therapy is not inadvertently interrupted due to the containers 112 being full and/or the urine system 110 being unable to accept urine output. In some embodiments, the treatment procedures described herein result in relatively large amounts and/or rates of urine output (e.g., compared to conventional therapies), such that automatic switching between multiple urine containers is advantageous to minimize treatment interruptions. Additional details of the urine system 110 and multiple container 112, and associated devices and methods, can be found in U.S. application Ser. No. 17/659,393, filed Apr. 15, 2022, the disclosure of which was previously incorporated by reference herein.

As another example, the hydration system 120 can include multiple redundant hydration fluid sources 122, e.g., to ensure the hydration fluid infusion can continue without interruption for the entirety of a therapy session and/or to provide an additional time window for switching hydration fluid sources 122 without interrupting hydration fluid infusion. In such embodiments, the hydration system 120 can include a hydration control assembly (e.g., valves and/or other flow control components—not shown) operably coupled to the controller 140, and configured to switch the source of hydration fluid from a first fluid source 122 to a second fluid source 122. In such embodiments, the hydration control assembly can initially deliver hydration fluid from the first fluid source 122 to the patient P. The hydration control assembly can monitor whether the first fluid source 122 is empty or nearly empty, e.g., based on data from the fluid sensor 128 and/or other sensors associated with the hydration system 120. Once the hydration control assembly detects or determines the first fluid source 122 is empty or nearly empty (e.g., the remaining amount of hydration fluid is below a predetermined threshold), the hydration control assembly can switch to delivering hydration fluid from the second source 122. The switching process can be repeated such that fluid therapy is not inadvertently interrupted due to the fluid source 122 being empty and/or the hydration system 120 being unable to provide hydration fluid.

The process of switching the hydration fluid source 122 can be performed automatically, semi-automatically, or manually. In some embodiments, semi-automatic or manual switching between the first and second fluid sources 122 may be beneficial to ensure the hydration system 120 does not automatically infuse hydration fluid without user confirmation. In such embodiments, the hydration control assembly and/or controller 140 can output an alert asking the user to verify that the hydration fluid should be switched from the first fluid source 122 to the second fluid source 122. Upon switching to the second fluid source 122, the controller 140 can generate an alert to the user to indicate the first fluid source 122 is empty and needs to be replaced. Optionally, the hydration control assembly and/or controller 140 can implement a pre-approval procedure in which the user allows the hydration system 120 to automatically infuse a specified volume of additional hydration fluid. Once that volume has been delivered to the patient P, the user may need to provide re-approval before further automatic infusion of hydration fluid.

In some embodiments, the different fluid sources 122 of the hydration system 120 each provide the same type of hydration fluid. In other embodiments, however, some or all of the fluid sources 122 can provide different types of hydration fluid. The hydration fluids can differ from each other with respect to tonicity, composition, electrolyte content, etc. Depending on the patient's response to diuresis, the hydration system 120 can deliver multiple different hydration fluids to the patient P sequentially or concurrently. For example, if the patient's urine output indicates that the patient P has an electrolyte imbalance (e.g., a positive sodium balance), the hydration system 120 can switch to delivering a hydration fluid that would address the imbalance (e.g., a hydration fluid with lower sodium content). The switching can be performed using any of the techniques and/or devices described above. Accordingly, the particular fluid or fluids delivered to the patient P can be tailored to the patient's particular clinical state and/or response to treatment.

In yet another example, the diuretic system 130 can include multiple redundant diuretic sources 134, e.g., to ensure the diuretic delivery can continue without interruption for the entirety of a therapy session and/or to provide an additional time window for switching diuretic sources 134 without interrupting diuretic delivery. For example, if a first diuretic source 134 (e.g., a first syringe or container) is spent, the diuretic can continue to be supplied (e.g., without substantial interruption) via a second diuretic source 134 (e.g., a second syringe or container). The second diuretic source 134 can be connected to the console 105, and can be operably coupled to a sensor configured to detect the presence of the second diuretic source 134 (e.g., a location sensor, optical sensor, weight sensor, etc.). Accordingly, the diuretic system 130 can switch to the second diuretic source 134 if the first diuretic source 134 is empty or nearly empty, and the second diuretic source 134 is present.

In some embodiments, the diuretic system 130 includes two independent diuretic pumps each including its own diuretic source 134. For example, the diuretic system 130 can include syringe pumps each fluidly coupled to its own syringe filled with diuretic. In some cases, such syringes may only be filled by pharmacists or other health care professionals, and thus may not be readily replaced (e.g., in less than a few hours) by the user. When the diuretic system 130 and/or controller 140 detects that the first diuretic source 134 is empty or nearly empty (e.g., below a predetermined threshold), the diuretic supply can be switched (e.g., automatically or manually) to a second diuretic source 134. In some embodiments, the diuretic system 130 can include one or more sensors configured to detect whether a backup syringe pump is available for use. The switching process can include stopping a first syringe pump fluidly coupled to the first syringe, and starting a second syringe pump fluidly coupled to the second syringe. In other embodiments, the diuretic system 130 includes a single diuretic pump (e.g., syringe pump) connected to two diuretic sources 134. In such embodiments, case switching between the first and second diuretic sources 134 can involve using a diuretic control assembly (e.g., valves and/or other flow control components) to switch the diuretic pump from delivering diuretic from the first diuretic source 134 to the second diuretic source 134. The switching process can be repeated such that fluid therapy is not inadvertently interrupted due to the diuretic source 134 being empty and/or the diuretic system 130 being unable to provide diuretic.

The process of switching the diuretic source 134 can be performed automatically, semi-automatically, or manually.

In some embodiments, manual or semi-automatic switching between the first and second diuretic sources 134 may be beneficial to ensure the diuretic system 130 does not automatically infuse a large volume of diuretic without user confirmation. In such embodiments, the controller 140 can output an alert asking the user to verify that the diuretic should be switched from the first diuretic source 134 to the second diuretic source 134. Upon switching to the second diuretic source 134, the controller 140 can generate an alert to the user to indicate the first diuretic source 134 is empty and needs to be replaced. Optionally, the controller 140 can predict a time point and/or time range when the first diuretic source 134 will be empty (e.g., based on the diuretic dosage rate), and can output a notification so the user can order or otherwise prepare a replacement diuretic source 134 before the first diuretic source 134 runs out. Moreover, the diuretic control assembly and/or controller 140 can implement a pre-approval procedure in which the user allows the diuretic system 130 to automatically delivery a specified additional dosage of diuretic. Once that dosage has been delivered to the patient P, the user may need to provide re-approval before further automatic delivery of diuretic.

In some embodiments, the different diuretic sources 134 of the diuretic system 130 each provide the same type of diuretic. In other embodiments, however, some or all of the diuretic sources 134 can provide different types of diuretics. Depending on the patient's response to diuresis, the diuretic system 130 can deliver multiple different diuretics to the patient P sequentially or concurrently. For example, the diuretic system 130 can initially deliver a first diuretic to the patient P from a first diuretic source 134. If the patient P responds poorly to the first diuretic (e.g., the urine output rate does not increase or increases very slowly), the diuretic system 130 can switch to delivering a second, different diuretic from a second diuretic source 134. The diuretic system 130 can continue delivering the first diuretic concurrently with the second diuretic, or can terminate delivery of the first diuretic when the second diuretic is delivered. The switching can be performed using any of the techniques and/or devices described above. As another example, if the patient P does not respond well to a single diuretic, the diuretic system 130 can simultaneously administer multiple diuretics to the patient P. The ratio of the different diuretics can be varied as appropriate to elicit a suitable urine output rate. In other embodiments, however, rather than automatically administering additional diuretics, the diuretic system 130 can output a notification recommending that the user manually administer a different diuretic to the patient P and/or requesting that the user approve administration of a different diuretic, which may be beneficial for patient safety.

Figure 2A:
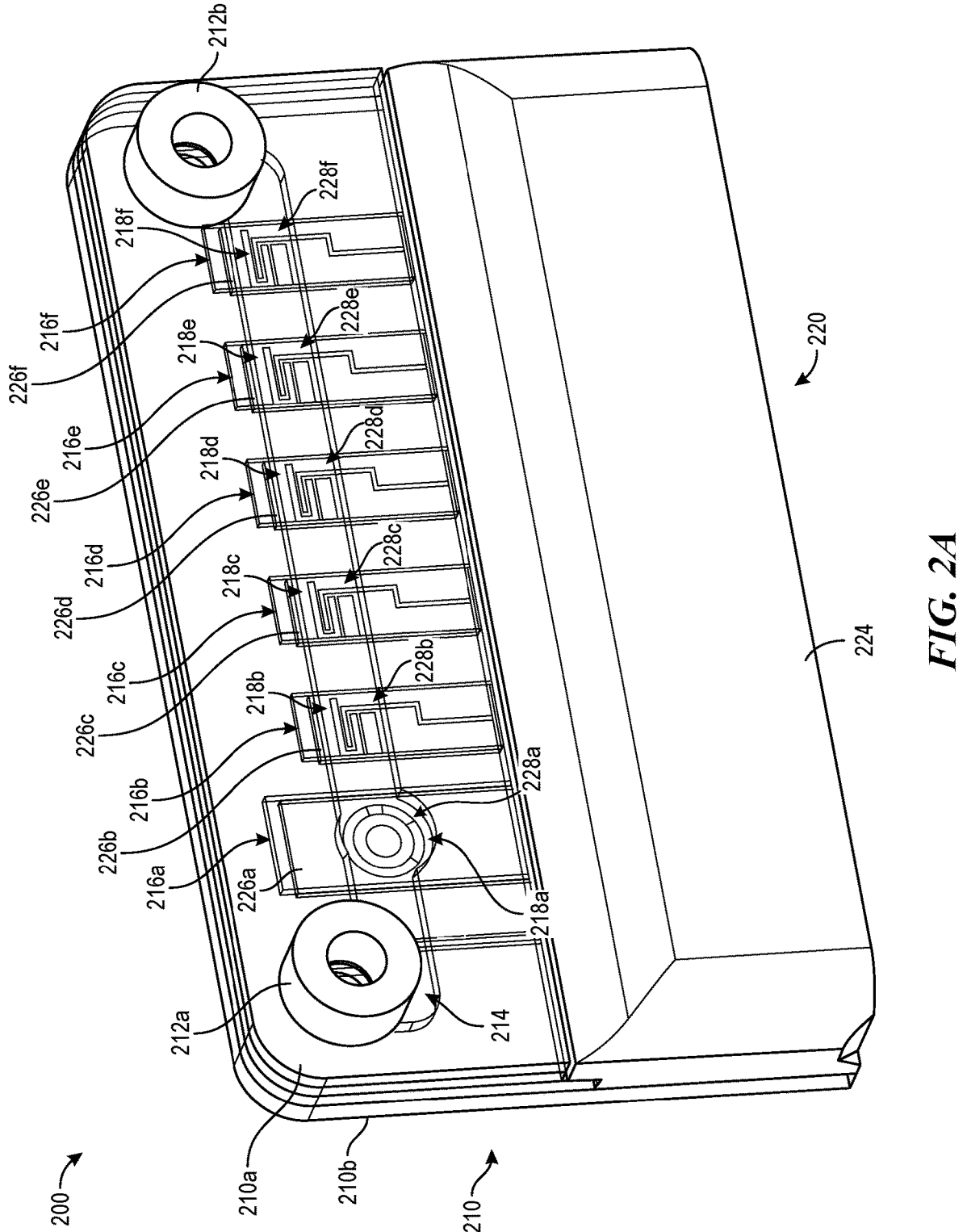
FIGS. 2A and 2B are perspective and exploded views, respectively, of a urine flow cartridge configured in accordance with embodiments of the present technology.
Figure 2B:
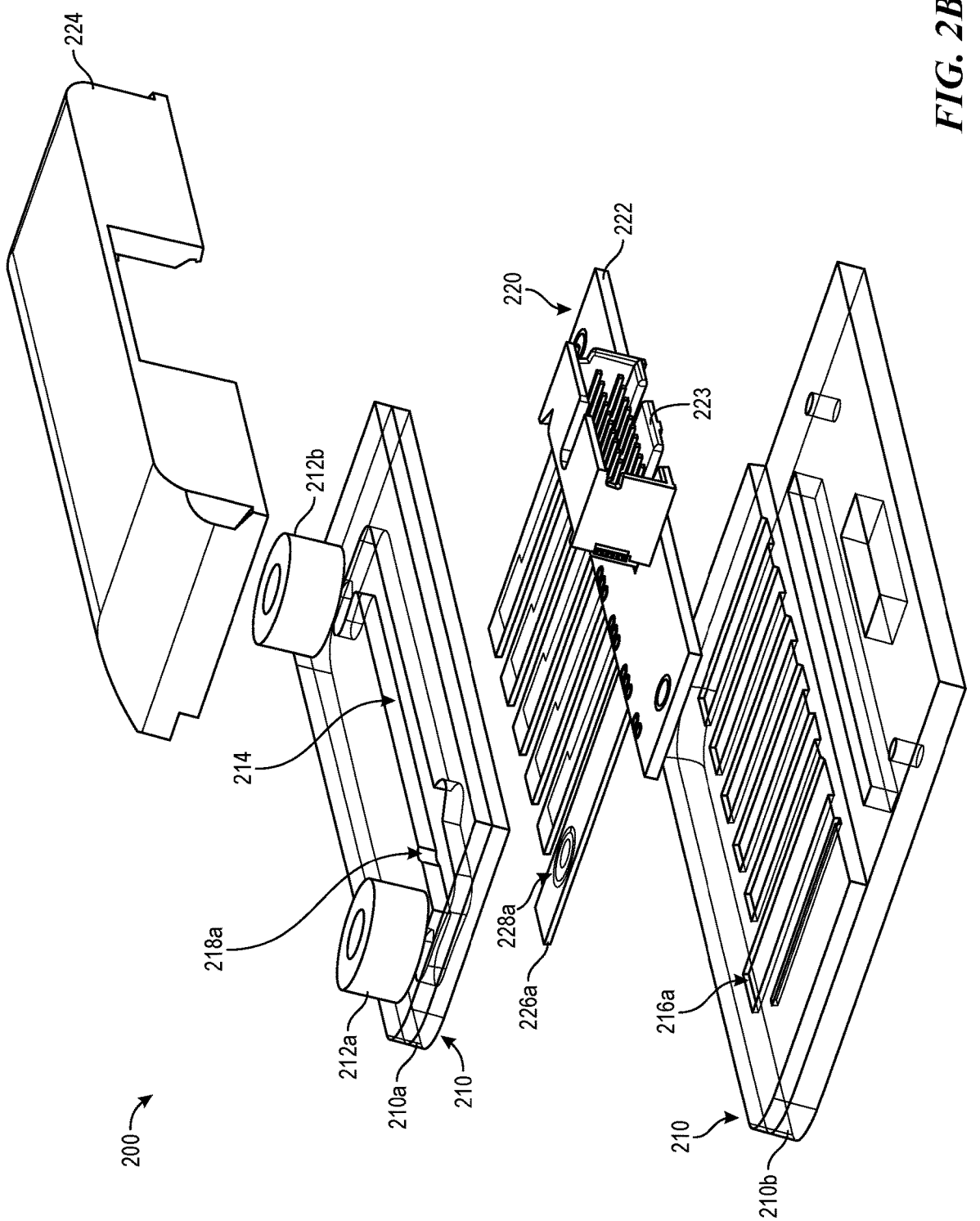

II. Measuring and/or Detecting Analytes in Urine, and Associated Systems, Devices and Methods FIGS. 2A and 2B are perspective and exploded views, respectively, of a urine flow cartridge 200 configured in accordance with embodiments of the present technology. The urine flow cartridge 200 can also be referred to as "cartridge 200," "urine cartridge 200," "flow cartridge 200," "sensing cartridge 200," "integrated cartridge 200," "flow cell 200," and the like. At least some aspects of the cartridge 200 can be generally similar or identical in structure and/or function to the cartridge 101 of FIG. 1.

Referring to FIGS. 2A and 2B together, the cartridge 200 can include a flow subassembly 210, a sensing subassembly 220, and a cover portion 224. The flow subassembly 210 can include a body formed from one or more plates. In the illustrated embodiment, the flow subassembly 210 includes a first (e.g., upper) plate 210*a* and a second (e.g., lower) plate 210*b*. In other embodiments, the flow subassembly 210 can include a single plate. The cartridge 200 can be used in a vertical, horizontal, and/or other orientation, and, as such, flow through the cartridge 200 can be generally insensitive to the orientation of the cartridge 200. In some embodiments, the cartridge 200 is intended for single-patient use (e.g., to avoid cross contamination).

The first plate 210*a* can include one or more fluid inlets 212*a* ("fluid inlet 212*a*"), one or more fluid outlets 212*b* ("fluid outlet 212*b*"), and one or more flow channels 214 ("flow channel 214") that fluidly couple the fluid inlet 212*a* to the fluid outlet 212*b*. The fluid inlet 212*a* can be configured to receive a fluid (e.g., urine) from a patient (via, e.g., the fluid line 119 of FIG. 1), and the channel 214 can define a flow path within the cartridge 200 through which the fluid flows. The fluid outlet 212*b* can be fluidly coupled to a fluid collection component (e.g., the container 112 in FIG. 1), or any other suitable fluid outflow location, such that the fluid can exit the cartridge 200 via the outlet 212*b*. In some embodiments, the outlet 212*b* can be omitted and the cartridge 200 can be configured to collect urine within an integral urine collection component fluidly coupled to the channel 214 downstream from the fluid inlet 212*a*.

The second plate 210*b* can be adhered or releasably coupled to the first plate 210*a* using one or more mechanical fasteners, adhesives, male/female coupling components, and/or any other suitable coupling process or technique. The second plate 210*b* can include sensor slots 216 that are fluidly coupled to and/or overlap portions of the flow channel 214 when the second plate 210*b* is coupled to the first plate 210*a*. For example, when the second plate 210*b* is coupled to the first plate 210*a*, the sensor slots 216 can form at least a portion of a side or surface of the flow channel 214, such that the fluid that flows through the channel 214 can interact with one or more objects (e.g., sensors) positioned within the sensor slots 216 and/or the sensing zones 218, as described in detail below.

In the illustrated embodiment, the second plate 210*b* includes six sensor slots 216*a-f*, e.g., a first sensor slot 216*a*, a second sensor slot 216*b*, a third sensor slot 216*c*, a fourth sensor slot 216*d*, a fifth sensor slot 216*e*, and a sixth sensor slot 216*f*. In other embodiments, the second plate 210*b* can include more or fewer sensor slots 216. Each of the sensor slots 216 can overlap with a portion of the flow channel 214 to define a corresponding sensing chamber or zone 218. In the illustrated embodiment, for example, the first sensor slot 216*a* overlaps the flow channel 214 to define a first sensing zone 218*a* downstream from the inlet 214*a*, the second sensor slot 216*b* overlaps the flow channel 214 to define a second sensing zone 218*b* downstream from the first sensing zone 218*a*, the third sensor slot 216*c* overlaps the flow channel 214 to define a third sensing zone 218*c* downstream from the second sensing zone 218*b*, the fourth sensor slot 216*d* overlaps the flow channel 214 to define a fourth sensing zone 218*d* downstream from the third sensing zone 218*c*, the fifth sensor slot 216*e* overlaps the flow channel 214 to define a fifth sensing zone 218*e* downstream from the fourth sensing zone 218*d*, and the sixth sensor slot 216*f* overlaps the flow channel 214 to define a sixth sensing zone 218*f* downstream from the fifth sensing zone 218*e* and/or upstream from the outlet 212*b*. In other embodiments, the cartridge 200 can include more or fewer sensing zones 218. As described in detail herein, each of the sensing zones 218 can be configured to sense and/or measure one or more respective properties of the urine flowing therethrough.

The sensing subassembly 220 can include a body 222 (FIG. 2B), one or more sensor tabs 226 extending from the body 222, and one or more sensing components or sensors 228*a-f* (collectively referred to as "sensors 228") (FIG. 2A). An individual one of the sensors 228 can be on or carried by a corresponding sensor tab 226*a-f* (collectively referred to as "sensor tabs 226"). In the illustrated embodiment, for example, one or more first sensors 228*a* are carried by a first sensor tab 226*a*, one or more second sensors 228*b* are carried by a second sensor tab 226*b*, one or more third sensors 228*c* are carried by a third sensor tab 226*c*, one or more fourth sensors 228*d* are carried by a fourth sensor tab 226*d*, one or more fifth sensors 228*e* are carried by a fifth sensor tab 226*e*, and one or more sixth sensors 228*f* are carried by a sixth sensor tab 226*f*. For illustration purposes, only the first sensors 228*a* and the first sensor tab 226*a* are labeled in FIG. 2B. In other embodiments, the sensing subassembly 220 can include more or fewer sensor tabs 226, and individual ones of the sensor tabs 226 can include any suitable number of sensors 228. As described in detail below, each of the sensors 228 can be configured to generate sensor data associated with one or more properties (e.g., electrical, chemical, and/or physical characteristics) of the patient's urine, e.g., while the urine is flowing through the respective sensing zone 218 of the channel 214. For example, the first sensor 228*a* can generate first sensor data, the second sensor 228*b* can generate second sensor data, and so on.

Each of the sensor tabs 226*a-f* can be received (e.g., slidably received) and/or otherwise positioned within a corresponding one of the sensor slots 216*a-f*. In the illustrated embodiment, for example, the first sensor tab 226*a* is configured to be positioned within the first sensor slot 216*a*, and each of the second through sixth sensor tabs 226*b-f* are configured to be positioned within a corresponding one of the second through sixth sensor slots 216*b-f*, respectively. When the sensor tabs 226 are positioned within the corresponding sensor slots 216, the sensors 228 on the sensor tabs 226 are configured to be aligned with and/or at least partially overlap the flow channel 214 and the sensing zones 218. In the illustrated embodiment, for example, when the first sensor tab 226*a* is positioned within the first sensor slot 216*a*, the first sensors 228*a* are aligned with and/or at least partially overlap at least the portion of the flow channel 214 that corresponds to the first sensing zone 218*a*. Additionally, each of the second through sixth sensors 226*b-f* correspond to the second through sixth sensing zones 218*b-f*.

As shown in FIG. 2B, the sensing subassembly 220 can include one or more electrical connectors 223. Each of the electrical connectors 223 can be communicatively coupled to one or more of the sensors 228 and configured to receive sensor data therefrom and/or transmit the sensor data to one or more other components of the system (e.g., the system 100 of FIG. 1), such as a processor (e.g., the processor 140 of the system 100), a remote database, and/or a server communicatively coupled to the system. Additionally or alternatively, the electrical connectors 223 can releasably couple the cartridge 200 to a portion of the system (e.g., the console 105 of FIG. 1).

In some embodiments, the sensing subassembly 220 can be releasably coupled to the flow subassembly 210, and/or positioned at least partially between the first plate 210*a* and the second plate 210*b* such that coupling the first and second plates 210*a-b* secures the sensing subassembly 220 to the flow subassembly 210. In such embodiments, individual ones of the sensor tabs 226*a* of the sensing subassembly 220 can be aligned with the corresponding sensor slots 216a of the second plate 210b before coupling the first plate 210a to the second plate 210b.

In operation, the cartridge 200 may monitor and/or measure, via the sensors 228, the patient's urine (e.g., in real time) to determine the concentration of analytes, including sodium ions, potassium ions, ammonium ions, urea, glucose, lactate, creatinine, oxygen tension, hormones, administered drugs, and/or furosemide). Additionally or alternatively, the cartridge 200 may monitor and/or determine, via the sensors 228, electrical properties of the analytes via a combination of amperometric, potentiometric, voltametric, and/or conductometric readings made in the sensing zones 218.

Urine can flow from the patient to the cartridge 200 via a non-return valve fluidly coupled to the inlet 212a. In some embodiments, the sensors 228 are activated when electrodes and/or electrical sensors within the cartridge 200 are shorted by the urine flowing therebetween. The sensors 228 may be configured such that the urine does not dissolve, sweep away, or remove the functional materials (e.g., ionophores, enzymes, antibodies, etc.) from the sensors 228. The raw electrochemical signals can be converted into the final analyte concentrations using the calibration factors associated with the cartridge 200 and transmitted to the cartridge (e.g., via the controller 140 of FIG. 1). In some embodiments, for example, the calibration factors can be stored as one or more RFID tags, QR codes, bar codes, or other data storage media, which can be "read" by the cartridge reader and transmitted to the controller 140 and/or the cartridge 200. The calibration factors can be associated with, for example, temperature, flow rate and/or other properties associated with operation of the sensors 228 and/or cartridge 200. The individual sensors 228 can be configured to be responsive to the urine proximate thereto (e.g., above) such that the results and measurements can be considered in real time.

The cartridge 200 can have various flow modes, including (i) a continuous flow mode in which fresh urine flows over the sensors, (ii) a stop-flow mode in which the sample flows onto and stops over the sensors 228 (e.g., via one or more flow control devices, as described in detail with reference to FIG. 5), and/or (iii) a recirculation flow mode in which the sample flows multiple times over one or more of the sensors 228 and/or through one or more of the sensing zones 218 and/or channels 214.

The sensors 228 can include one or more chemical sensors, physical sensors (e.g., temperature sensors or flow sensors), electrical sensors, electrochemical sensors, and/or other suitable sensors. As described in more detail with reference to FIGS. 3-5, the flow path of urine through the channel 214 and over the sensors 228 can be serial, parallel, or a combination thereof in two or three dimensions. In embodiments including parallel flow, the urine stream may be split into parallel streams and analyzed by sensors 228 within each of the parallel channels. In such embodiments, the cartridge 200 may enable flushing solutions and/or calibration solutions to selectively flow through individual flow channels 214, and the sensors 228 may include a number of reagents. For example, the reagents can be printed (e.g., via analogue/screen printing or digital printing) or otherwise deposited on the sensors 228, and can be configured to react with and/or be solubilized by the urine within the sensing zone 218. In some embodiments, the deposited reagent prints can have at least one dimension on the single millimeter scale or less when dried.

The sensors 228 can be configured to have responses independent of chloride concentration. In this regard, electrochemical sensors can have a signal dependent on both the analyte of interest measured on the working electrode and the concentration of chloride at the reference electrode. Sensors can perform adequately when the concentration of chloride within patient samples (e.g., serum, blood, or plasma interstitial fluid) is fairly non-variant. However, for samples such as urine in which the chloride concentration is variable, the sensing system may either compensate for the chloride concentration or be inherently chloride insensitive. Accordingly, embodiments of the present technology can utilize reference electrodes that are chloride insensitive.

The sensors 228 within the cartridge 200 can be recalibrated using one or more calibration solutions. These calibration solutions can be applied on the sensors 228, and contain several analytes at known concentrations, conductivity, and/or pH. The sensors 228 can be calibrated based on the known concentration of analytes flowing through the cartridge 200 and the raw signals from the sensors 228. For example, the controller 140 (FIG. 1) can make calibration adjustments for certain parameters (e.g., sensor sensitivity and/or sensor offset). Physical and chemical parameters such as flow rate, temperature, pH, etc., can be used as part of the processing of other signals, such as the adjustment of calculated glucose concentration based on the pH, flow rate, and/or temperature within the flow cell. In some embodiments, the cartridge 200 can include heaters or other heating and/or cooling means to control temperature of the cartridge 200, e.g., at the sensing zones 218. In such embodiments, the temperature of the corresponding areas of the cartridge 200 can be actively controlled to be between 20-40° C. Such temperature control can improve assay sensitivity, and thereby accuracy, such that the cartridge 200 can be used in ambient conditions where the assay would otherwise not operate.

Individual measurements or a combination of measurements made within the cartridge 200 may be presented to the clinician to help inform treatment. In addition, measurements can be combined to provide scores to assist medical decisions. In some embodiments, the measured parameters can be used in a closed loop control to effect devices (e.g., pumps) to automatically or semi-automatically monitor and control the therapy, as described in detail herein.

Measuring ions, such as sodium and chloride, within the urine may provide objective indications of the patient's total body water, sometimes referred to as hydration. For example, a high sodium concentration within the urine may indicate a low or insufficient infusion of aqueous solution to the patient, whilst a low sodium concentration may indicate a high or excess infusion of aqueous solution to the patient. Such real-time data is expected to enable more accurate control of fluid therapies.

In some embodiments, the cartridge 200 can perform all or substantially all the functions involved with collecting and analyzing urine with little or no manual manipulation or intervention by the user or clinician. Additionally, or alternatively, the cartridge 200 can eliminate manual handling of the urine and/or moving components of the cartridge 200, while also protecting the urine from accidental contamination and/or guiding the sample through the channels 214 and chambers 218 without entrapping air. Moreover, since the urine flow channel 214 can be enclosed and not exposed to the atmosphere, embodiments of the present technology can reduce the risk of exposure and/or prevent evaporation, which could affect corresponding concentration(s).

In some embodiments, the cartridge 200 includes electrode materials selected to maximize or optimize electrochemical interaction with the analytes of interest. The detection of the analytes can be made by either destructive or non-destructive means. Contributions to the total measured signal due to non-specific sources (e.g., chemical interferences, electrical interferences, and/or sensor variations) can be measured and accounted for in the final signal. In some embodiments, this improves the ability of the cartridge 200 to quickly and/or accurately detect the presence and/or concentration of the analytes of the urine flowing through the cartridge 200.

In some embodiments, the dimensions of the channel 214 of the cartridge 200 are designed to control whether the flow of urine through the channel 214 is turbulent or laminar. In some embodiments, the channel 214 has a width less than 10 mm and height less than 5 mm. In these and other embodiments, the channel dimensions may be minimized to reduce the total sample of urine necessary for the assays, whilst remaining at a scale that allows for mass low-cost production.

With many sensing-based systems, the magnitude of the final signal and the sensitivity of the signal to the analyte or measurement of interest can vary between sensors. Embodiments of the present technology attempt to reduce or eliminate such variability, e.g., by enabling calibration of the cartridge 200 at the point of use. Additionally, changes to the sensitivity of the cartridge 200 due to aging can be calibrated for by a time-based aging model based upon the age of the cartridge 200.

Although in the embodiment illustrated in FIGS. 2A and 2B the sensors 228 are carried by the sensor tabs 226a that are positioned within corresponding ones of the sensor slots 216, in other embodiments individual ones of the sensors 228 can have other configurations. For example, individual ones of the sensors 228 can be fixed within the corresponding sensor slot 216, such that the corresponding sensor tab 226 can be omitted and/or individual ones of the sensors 228 can be integrated into the second plate 210b. Additionally, or alternatively, individual ones of the sensors 228 can be aligned with and/or coupled to one or more interior surfaces of the channel 214. for example, individual ones of the sensors 228 can be aligned with and/or coupled to one or more of the sides and/or the upper surface of the channel 214. Accordingly, in some embodiments individual ones of the sensing zones 218 can include one or more first sensors positioned on a first side of the sensing zone 218, such as the lower surface of the channel 214, and one or more second sensors positioned on a second side of the sensing zone 218 that is different than the first side, such as the upper surface of the channel 214.

Figure 3:
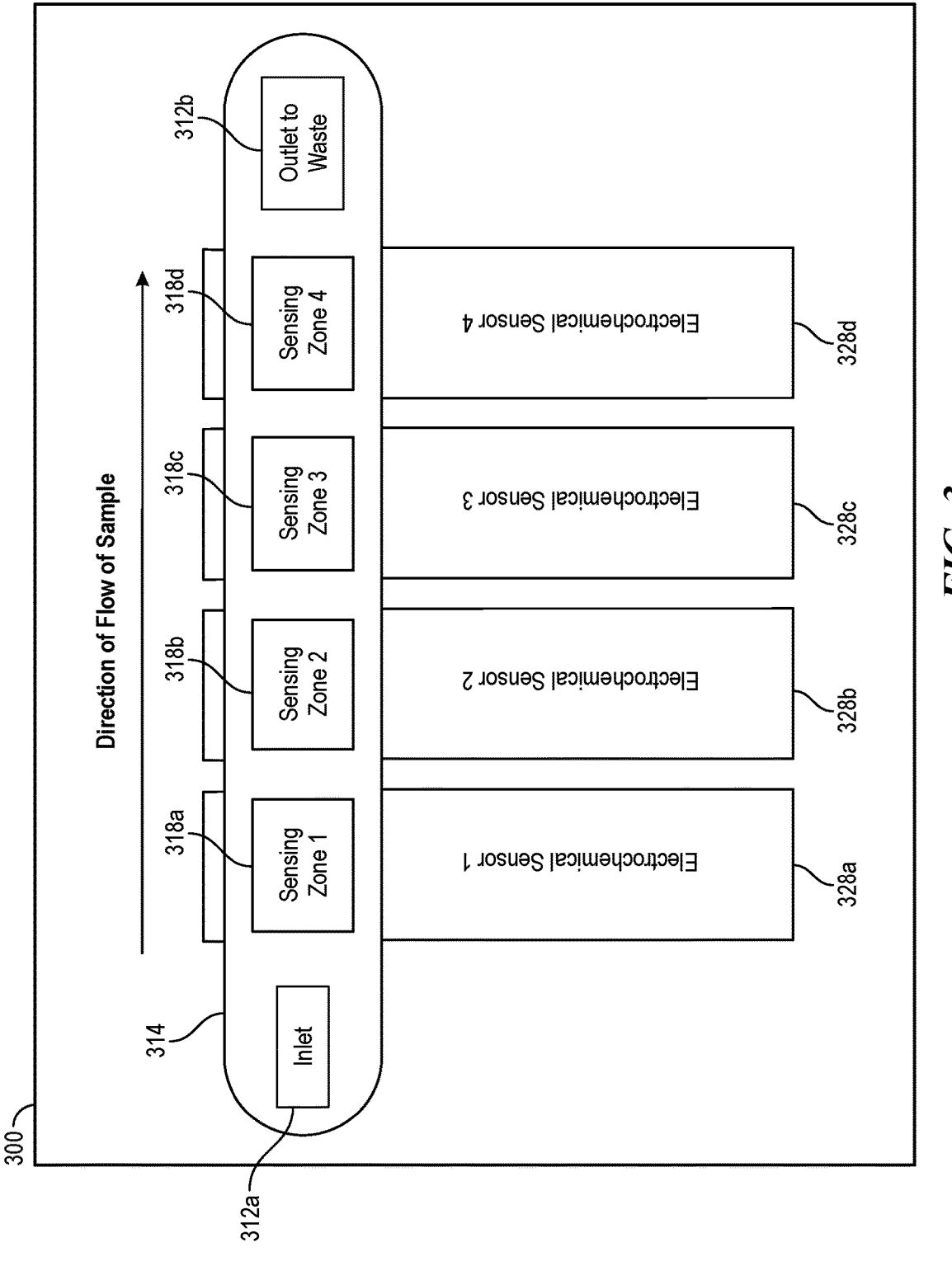
FIGS. 3-5 are partially schematic illustrations of respective cartridges configured in accordance with embodiments of the present technology.
Figure 4:
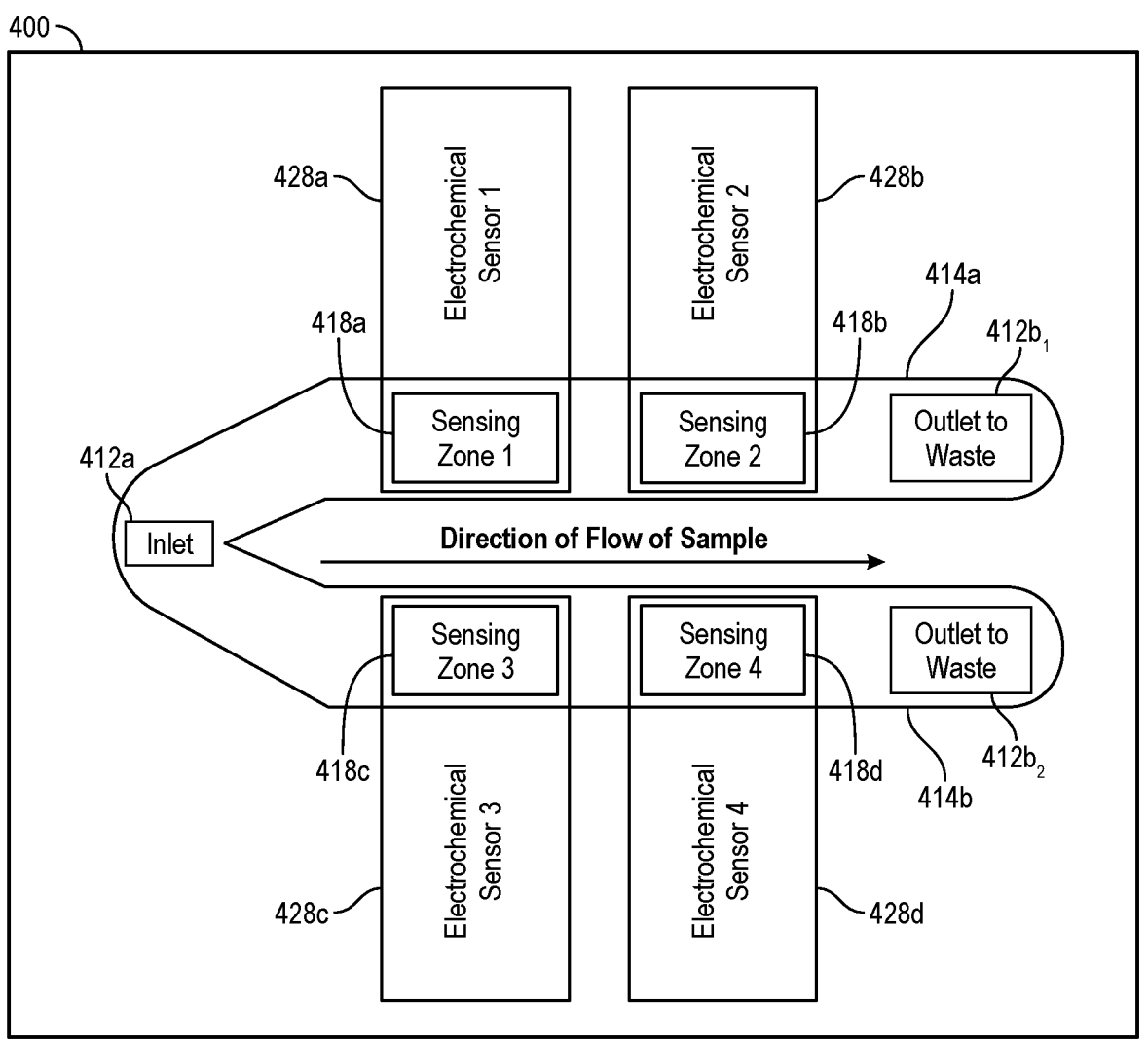
Figure 5:
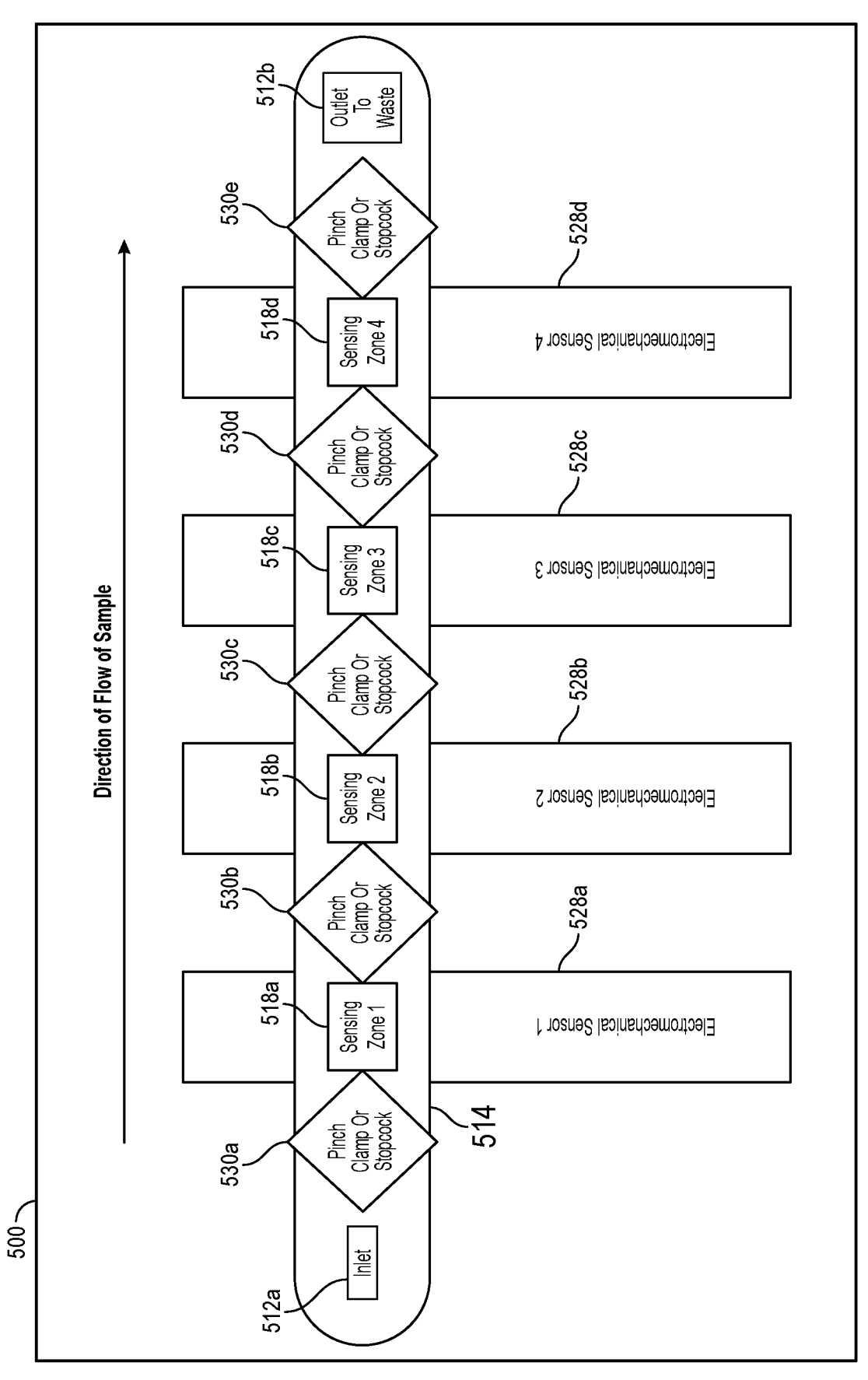

FIGS. 3-5 are partially schematic illustrations of respective cartridges 300, 400, 500, respectively, configured in accordance with embodiments of the present technology. At least some aspects of the cartridges 300, 400, 500 of FIGS. 3-5 can be generally similar or identical in structure and/or function to one or more aspects of the cartridge 200 of FIGS. 2A and 2B. For the discussion of FIGS. 3-5, like reference numbers and/or names (e.g., inlet 314a, 414a, 514a versus the inlet 214a of FIGS. 2A and 2B) are used to indicate aspects of the respective cartridges 300, 400, 500 that can be generally similar or identical to each other and/or the cartridge 200 of FIGS. 2A and 2B.

FIG. 3 illustrates a cartridge 300 having a channel 314 that defines a flow path between an inlet 312a and an outlet 312b. The sensors 328a-d and the corresponding sensing zones 318a-d are arranged in series along the length of the channel 314. Accordingly, urine can be received within the channel 314 from the patient via the inlet 312a, flow through the sensing zones 318a-d, and interact with the associated sensors 328a-d in series, for example, via the first sensing zone 318a and sensor 328a, followed by the second sensing zone 318b and second 328b, and so on. Once the urine reaches the outlet 312b, the urine can flow out of the cartridge 300 and into, for example, a container (e.g., the container 112 of FIG. 1) for collection and/or disposal, or any other suitable fluid outflow location.

FIG. 4 illustrates a cartridge 400 including an inlet 412a, a first channel 414a, a first outlet 412b coupled to the inlet 412a via the first channel 414a, a second channel 414b, and a second outlet 412c coupled to the inlet 412a via the second channel 414b. Flow through the first and second channels 414a-b is in parallel. Both the first and second channels 414a-b can include respective sensing zones 418 and sensors 428. In the illustrated embodiment, for example, the first channel 414a includes a first sensing zone 418a with one or more first sensors 428a and a second sensing zone 418b with one or more second sensor 428b, and the second channel 414b includes a third sensing zone 418c with one or more third sensors 428c and a fourth sensing zone 418d with one or more fourth sensors 428d. Accordingly, the first and second sensing zones 418a, 418b and sensors 428a, 428b are parallel to the third and fourth sensing zones 418c, 418d and sensors 428c, 428d. In some embodiments, the cartridge 400 can include more than two channels in parallel (e.g., three channels, four channels, five channels, etc.).

The parallel arrangement of sensors 428a-d within the channels 414a-b may reduce the potential of interference or chemical mixing between sensors 428a-d. For example, in a single path flow cell a glucose sensor, for example could chemically interfere with a lactate sensor if the lactate sensors were downstream of the glucose sensor. Without being bound by theory, this is because the glucose sensor can produce relatively high amounts of hydrogen peroxide, which can flow onto and interfere with a lactate sensor downstream of the glucose sensor. The parallel channels 414a-b of the cartridge 400 are positioned in different flow paths (i.e., one in each flow path 414a, 414b) such that hydrogen peroxide or other compound generated by one of the sensors does not flow onto or otherwise interfere with the operation of the other one of the sensors.

FIG. 5 schematically illustrates a cartridge 500 with flow control devices or valves 530 between individual sensors 528 in accordance with various embodiments of the present technology. In the illustrated embodiment, the cartridge 500 includes four sensors 528a-d (e.g., electromechanical sensors), each associated with a respective sensing zone 518a-d. In some embodiments, the cartridge 500 includes more or fewer sensors (e.g., five sensors, eight sensors, three sensors, etc.). The cartridge 500 also includes five valves 530a-e (e.g., pinch clamps or stopcocks) that fluidically isolate the sensing zones 518a-d from each other and/or from the inlet 512a or outlet 512b of the cartridge 500. Each valve 530a-e can be independently actuated (e.g., opened and closed) to selectively permit fluid flow along the cartridge 500 (e.g., along the direction indicated by the arrow) and across the various sensing zones 518a-d. As previously described, the valves 530a-e can provide various advantages, such as reducing cross communication and/or other interference between sensors, as well as reducing variability in sensor performance that may occur when the cartridge 500 is fluidically connected to the patient's body. For example, some types of tests can change the chemistry of the fluid under test and influence other sensors 528. Additionally or alternatively, some sensors 528 can apply a voltage to the test sample to perform the assay, such that other sensors placed in the same solution may see cross communication between the sensors; separating the sensors can minimize or eliminate this cross communication. Some sensors 528 are highly sensitive to static and high frequency energy, and valving these sensors 528 from the patient can decrease the transfer of static to the sensors and/or reduce or elimination the creation of spikes or other noise in the data. In some embodiments, one or more of the sensors 528 can require a static analyte that does not flow thereover.

The various cartridges described herein with reference to FIGS. 1-5 can be used in a wide variety of applications. In some embodiments, for example, the cartridges herein are used to monitor the urine output of a patient undergoing a fluid management therapy, such as a therapy to treat a fluid overload condition. As previously described, to treat fluid overload, patients can be administered a diuretic drug which induces and/or increases urine production, such as described previously with reference to FIG. 1. Diuretics can be given orally as a pill or as an intravenous (IV) injection. IV diuretics can be used when oral diuretics are no longer effective and/or able to be absorbed.

One or more of the cartridges described herein can be used in combination with various systems, device, and methods for managing fluid levels of a patient, such as the system 100 of FIG. 1 and/or any of the embodiments described in U.S. patent application Ser. No. 17/112,925, filed Dec. 4, 2020, the disclosure of which is incorporated herein by reference in its entirety. In some embodiments, for example, a system for managing fluid levels is configured to (1) monitor and/or collect a patient's urine output, (2) administer a diuretic to the patient to elicit a desired urine output rate, and/or (3) infuse a hydration fluid into the patient to maintain a desired hydration level during therapy. The sensor data from the cartridges described herein can be used to monitor and/or guide the fluid management therapy implemented by the system. For example, the system can receive and use analyte measurements generated by the devices herein (e.g., levels of creatine, sodium, oxygen, etc.) in combination with measurements of the patient's urine output rate to determine any of the following: whether the fluid management therapy should be initiated, paused, or terminated; whether the diuretic dosage and/or dosage rate should be increased, decreased, or maintained; whether the hydration fluid infusion rate should be increased, decreased, or maintained; whether the clinician should be notified of the patient's condition (e.g., the patient is in a declining or dangerous state); and/or suitable combinations thereof.

III. Conclusion

The present technology is illustrated, for example, according to various aspects described below as numbered examples (1, 2, 3, etc.) for convenience. These examples do not limit the present technology. It is noted that any of the dependent examples may be combined in any combination, and placed into a respective independent example.

EXAMPLES

1. A flow cartridge configured for analyzing urine, the cartridge comprising:
   a flow cell configured to collect and measure a flow of urine, the flow cell comprising one or more sensing zones configured to detect analytes within the urine and perform one or more physical measurements; and
   a urine inlet configured to receive the flow of urine, the urine inlet being integrated with the one or more sensing zones, wherein the urine inlet is configured so that urine passes from the urine inlet to the one or more sensing zones.

2. The cartridge of example 1, wherein the one or more physical measurements include temperature and flow rate.

3. The cartridge of example 1 or example 2, wherein the flow cell is configured so that a final assay is performed at an uncontrolled temperature.

4. The cartridge of example 1 or example 2, wherein the flow cell is configured so that a final assay is performed at a controlled temperature.

5. The cartridge of example 4, wherein the flow cell comprises one of an Ohmic heater or a Peltier device configured to control the temperature.

6. The cartridge of any of examples 1-5, wherein the flow cell is configured so that measurement of the urine is performed within a single device.

7. The cartridge of any of examples 1-6, wherein the flow cell is configured so that during operation, the urine is shielded or shaded from ambient light to reduce photochemical reactions that would otherwise adversely affect the measurement of the analytes.

8. The cartridge of any of examples 1-7, wherein the flow cell is configured to mostly enclose the urine so that the urine is protected from accidental contamination.

9. The cartridge of any of examples 1-8, further comprising a combination of materials, membranes and polymers that exclude common interferences.

10. The cartridge of example 9, wherein the common interferences include ascorbic acid and acetaminophen.

11. The cartridge of any of examples 10, further comprising millimeter dimensioned electrodes configured to perform a final analysis of the urine.

12. The cartridge of any of examples 1-11, wherein the lengths of the electrodes are approximately 1 millimeter, and the widths of the electrodes are approximately 500 micrometers.

13. The cartridge of any of examples 1-12, wherein the flow cell is configured to perform electrochemical techniques.

14. The cartridge of any of examples 1-13, wherein the electrochemical techniques include one or more of amperometry, voltammetry, potentiometry, or conductimetry.

15. The cartridge of any of examples 1-14, wherein at least one sensing zone is configured so that a temperature in the at least one sensing zone is actively controllable to be between 20 to 40° C.

16. The cartridge of any of examples 1-15, wherein at least one sensing zone is configured to monitor a temperature that is usable to adjust other parameters that are also measured within the flow cell.

17. The cartridge of example 16, wherein the other parameters include chemical parameters.

18. The cartridge of any of examples 1-17, wherein the flow cell is configured to measure sodium ions.

19. The cartridge of any of examples 1-18, wherein the flow cell is configured to measure potassium ions.

20. The cartridge of any of examples 1-19, wherein the flow cell is configured to measure pH.

21. The cartridge of any of examples 1-20, wherein the flow cell is configured to measure urine conductivity.

22. The cartridge of any of examples 1-21, wherein the flow cell is configured to measure oxygen levels.

23. The cartridge of any of examples 1-22, wherein the flow cell is configured to measure hormone levels.

24. The cartridge of any of examples 1-23, wherein the flow cell is configured to measure a level of at least one drug.

25. The cartridge of example 24, wherein the at least one drug includes furosemide.

26. The cartridge of any of examples 1-25, further comprising a controller configured to adjust signals based on one or more of pH, temperature, specific gravity, or flow rate.

27. The cartridge of any of examples 1-26, wherein the flow cell is configured to make electrochemical based assay measurements in uncontrolled chloride concentration urine samples.

28. The cartridge of any of examples 1-27, wherein the flow cell is configured to be oriented vertically and horizontally in use.

29. The cartridge of any of examples 1-28, further comprising electrode materials having a maximum electrochemical activity towards predetermined analytes.

30. The cartridge of any of examples 1-29, further comprising electrodes with dimensions on the millimeter scale.

31. The cartridge of example 30, wherein the dimensions facilitate the electrodes to be made by a number of high-volume manufacturing techniques.

32. The cartridge of any of examples 1-31, further comprising a final chamber to receive the urine and enclose the urine on multiple sides, the final chamber having an output port for waste.

33. The cartridge of any of examples 1-32, wherein the cartridge is optimized to assist the flow of urine and minimize the formation of air bubbles.

34. The cartridge of any of examples 1-33, wherein the flow cell is configured to detect air bubbles and act upon interference effects of the air bubbles.

35. The cartridge of any of examples 1-34, wherein the sensing zone is configured to automatically start an assay once a sufficient volume of urine has entered the sensing zone.

36. The cartridge of any of examples 1-35, wherein the cartridge is configured to operate without any external intervention.

37. The cartridge of any of examples 1-36, wherein at least one of the sensing zones is an analyte sensing zone with a volume of less than 1 milliliter.

38. The cartridge of any of examples 1-37, wherein the at least one sensing zone has a defined height, width and depth configured to control the total volume of urine within a sensing chamber of the at least one sensing zone.

39. The cartridge of any of examples 1-38, further comprising many channels that have dimensions configured to make the flow of urine turbulent.

40. The cartridge of any of examples 1-39, further comprising many channels that have dimensions configured to make the flow of urine laminar.

41. The cartridge of any of examples 1-40, wherein the one or more sensing zones comprise one or more embed sensors that are configured to immediately detect analytes within urine or characterize the urine itself.

42. The cartridge of any of examples 1-41, further comprising one or more temperature monitoring zones.

43. The cartridge of any of examples 1-42, further comprising one or more zones that are temperature controlled.

44. The cartridge of example 43, wherein the one or more zones are configured to be held at the same temperature.

45. The cartridge of example 43, wherein the one or more zones are configured to be held at different temperatures.

46. The cartridge of any of examples 43-45, wherein the one or more zones are configured to change the temperature during the operation.

47. The cartridge of example 46, wherein the one or more zones are configured to control the temperature relative to ambient temperature.

48. The cartridge of example 46, wherein the one or more zones are configured to automatically change the temperature.

49. The cartridge of any of examples 1-48, wherein a single sensing zone is configured to measure more than one analyte or characteristic of the urine either in parallel or sequentially.

50. The cartridge of any of examples 1-49, further comprising channels configured to convey the urine.

51. The cartridge of example 50, wherein the channels have widths of less than 10 mm and heights less than 5 mm.

52. The cartridge of example 51, wherein the channel dimensions are minimized to reduce the volume of urine, whilst remaining at a scale that allows for mass low-cost production.

53. The cartridge of any of examples 1-52, wherein the device is configured for single patient use, to avoid cross contamination.

54. The cartridge of any of examples 1-53, wherein the flow cell is configured so that an expended sample of urine is mostly contained for safer final disposal.

55. The cartridge of any of examples 1-54, wherein the flow cell is configured to detect the analyte by a destructive process.

56. The cartridge of any of examples 1-55, wherein the flow cell is configured to detect the analyte by a non-destructive process.

57. The cartridge of any of examples 1-56, wherein the cartridge is configured to measure contributions to the total measured signal due to non-specific sources that include: chemical interferences, electrical interferences, sensor variations, and wherein the measured contributions are accounted for in a final signal.

58. The cartridge of any of examples 1-57, further comprising a number of reagents printed on sensors.

59. The cartridge of example 58, wherein the reagents are printed using analogue/screen printing or digital printing.

60. The cartridge of example 59, wherein the deposited reagent prints have at least one dimension on the single millimeter scale or less when dried.

61. The cartridge of any of examples 1-60, further comprising a data tag, which is readable by a reader.

62. The cartridge of example 61, wherein the data tag is RFID.

63. The cartridge of example 61 or example 62, wherein the reader is configured to transfer calibration factors and data of manufacture.

64. The cartridge of example 63, wherein the reader includes a time-based algorithm that accounts for any cartridge aging effects.

65. The cartridge of any of examples 1-64, wherein the cartridge is configured to monitor a patient over several days to track the patient's longitudinal response to clinical interventions.

66. The cartridge of any of examples 1-65, further comprising one or more valves configured to fluidically isolate at least some of the sensing zones from each other.

67. The cartridge of example 66, wherein the one or more valves include at least one valve configured to fluidically isolate at least some of the sensing zones from the urine inlet.

68. A flow cartridge for analyzing urine, the flow cartridge comprising:

a urine inlet configured to receive urine from a patient;

a urine outlet;

a channel fluidly coupled to the urine inlet and the urine outlet, wherein the channel includes sensing zones positioned between the urine inlet and the urine outlet; and sensors positioned downstream from the urine inlet and fluidly coupled to the channel, wherein individual sensors are aligned with a corresponding one of the sensing zones and operable to generate sensor data based on urine flow through the corresponding sensing zone.

69. The flow cartridge of example 68 wherein individual ones of the sensors include a chemical sensor, an electrochemical sensor, a temperature sensor, or a flow sensor.

70. The flow cartridge of example 68 or example 69 wherein one of the sensors is positioned to contact the urine within the corresponding sensing zone of the sensor.

71. The flow cartridge of any of examples 68-70 wherein the sensors include a first sensor downstream of the urine inlet, a second sensor downstream of the first sensor, and a third sensor between the second sensor and the outlet, wherein the first, second, and third sensors are arranged sequentially along a length of the channel.

72. The flow cartridge of any of examples 68-71 wherein the channel is a first channel, wherein the sensing zones include a first sensing zone, and wherein the sensors include a first sensor operable to generate first sensor data, the flow cartridge further comprising:

a second channel fluidly coupled to the urine inlet, a second sensor downstream of the urine inlet and fluidly coupled to the second channel, and a second sensing zone fluidly coupled to the urine inlet, wherein the second sensor is aligned with the second sensing zone and operable to generate second sensor data based on urine flow through the corresponding second sensing zone.

73. The flow cartridge of example 72 wherein the first channel is arranged in parallel to the second channel.

74. The flow cartridge of any of examples 68-73, further comprising a flow control device transitionable between (i) a first configuration in which the flow control device at least partially prevents urine flow into one of the sensing zones, and (ii) a second configuration in which the flow control device allows urine flow into one or more of the sensing zones.

75. The flow cartridge of example 74 wherein the flow control device includes a pinch clamp or a stopcock.

76. The flow cartridge of example 74 or example 75 wherein the flow control device is positioned between individual ones of the sensing zones.

77. The flow cartridge of any of examples 74-76 wherein the sensing zones include a first sensing zone and a second sensing zone downstream from the first sensing zone, and the flow control device is positioned between the first sensing zone and the second sensing zone.

78. The flow cartridge of any of examples 74-77 wherein the flow control device is positioned between the urine inlet and the sensing zones or between the urine outlet and the sensing zones.

79. A flow cartridge for analyzing urine, the flow cartridge comprising:

a urine inlet configured to receive a flow of urine;

a flow channel in fluid communication with the urine inlet and comprising sensing zones that are positioned in series relative to one another along a length of the flow channel; and a plurality of sensors in fluid communication with the flow channel and corresponding ones of the sensing zones, wherein each of the sensors is aligned with a corresponding one of the sensing zones, and wherein the sensors are each configured to measure a chemical parameter and/or a physical parameter of the flow of urine.

80. The flow cartridge of example 79 wherein:

the physical measurements include at least one of a temperature or a urine conductivity, and the chemical measurements include a concentration of at least one of sodium, potassium, chloride, lithium, pH, ammonia, urea, glucose, or lactate.

81. The flow cartridge of example 79 or example 80, further comprising:

a first plate including the urine inlet and the flow channel;

a second plate removably coupled to the first plate; and a sensing subassembly including the sensors, wherein the sensing subassembly is positioned between the first plate and the second plate.

82. The flow cartridge of example 81 wherein:

the second plate includes a plurality of sensor slots, the sensing subassembly includes a body and a plurality of sensor tabs extending from the body, and the sensor tabs each include a corresponding one of the sensors.

83. The flow cartridge of example 82 wherein the sensor slots are configured to receive the sensor tabs when the first plate is coupled to the second plate.

84. A method for analyzing urine from a patient, the method comprising:

receiving, within a channel of a flow cartridge, urine flow from a patient;

measuring, via two or more sensors at corresponding sensing zones of the channel, one or more properties of the patient's urine; and based on the measured properties, providing at least one of a diuretic or a hydration fluid to the patient.

85. The method of example 84 further comprising activating the sensing zone in response to the urine flow.

86. The method of example 85 wherein activating the sensing zone includes detecting, via one or more sensors positioned within the sensing zone, a start condition associated with the presence of urine within the sensing zone.

87. The method of any of examples 84-86 wherein the sensing zone is a first sensing zone and the one or more properties are one or more first properties, further comprising:

closing a valve positioned downstream of the first sensing zone to at least partially prevent urine flow into a second sensing zone downstream from the valve; and after determining the one or more first properties via the first sensing zone— opening the valve to allow the urine within the first sensing zone to flow into the second sensing zone; and determining, via the second sensing zone, one or more second properties of the patient's urine.

88. A fluid therapy system, comprising:

a first pump configured to provide a diuretic to a patient;

a second pump configured to provide a hydration fluid to the patient; and a urine system including— a fluid line fluidly coupled to the patient and configured to receive urine therefrom, and a urine cartridge fluidly coupled to the urine line, wherein the urine cartridge includes a flow channel and sensors positioned within the flow channel, wherein individual ones of the sensors are configured to generate sensor data based on the urine flowing through the channel.

89. The fluid therapy system of example 88 wherein individual ones of the sensors include a chemical sensor, an electrochemical sensor, a temperature sensor, or a flow sensor.

90. The fluid therapy system of example 88 or example 89 wherein one of the sensors is positioned to contact the urine as the urine flows through the flow channel.

91. The fluid therapy system of any of examples 88-90 wherein the sensors include a first sensor downstream of the fluid line, a second sensor downstream of the first sensor, and a third sensor downstream from the second sensor, wherein the first, second, and third sensors are arranged sequentially along a length of the flow channel.

92. The fluid therapy system of any of examples 88-91 wherein the flow channel is a first flow channel, wherein the sensors include a first sensor operable to generate first sensor data, the urine system further comprising:

a second channel fluidly coupled to the fluid line, a second sensor downstream of the fluid and fluidly coupled to the second flow channel, wherein the second sensor is operable to generate second sensor data based on urine flow through the corresponding second flow channel.

93. The fluid therapy system of example 92 wherein the first flow channel is arranged in parallel to the second flow channel.

94. The fluid therapy system of any of examples 88-93 further wherein the urine system further comprises a flow control device transitionable between (i) a first configuration in which the flow control device at least partially prevents urine flow into one of the sensing zones, and (ii) a second configuration in which the flow control device allows urine flow into one or more of the sensing zones.

95. The flow cartridge of example 94 wherein the flow control device includes a pinch clamp or a stopcock.

96. The flow cartridge of example 94 or example 95 wherein the flow control device is positioned between individual ones of the sensing zones.

97. The flow cartridge of any of examples 94-97 wherein the sensing zones include a first sensing zone and a second sensing zone downstream from the first sensing zone, and the flow control device is positioned between the first sensing zone and the second sensing zone.

98. The flow cartridge of any of examples 94-97 wherein the flow control device is positioned between the urine inlet and the sensing zones or between the urine outlet and the sensing zones.

99. A urine collection system, comprising:

a console configured to receive urine from a patient in a container; and a urine cartridge coupled to a console, the urine cartridge comprising— a urine inlet configured to receive a flow of urine from the patient;

a urine outlet fluidly coupled to the container;

a flow channel extending in fluid communication with the urine inlet and the urine outlet, and comprising a plurality of sensing zones, wherein the sensing zones are positioned in series relative to one another along a length of the flow channel;

a plurality of sensors in fluid communication with the flow channel and corresponding ones of the sensing zones, wherein each of the sensors is aligned with a corresponding one of the sensing zones, and wherein the sensors are each configured to measure a chemical parameter and/or a physical parameter of the flow of urine.

100. The urine collection system of example 99 wherein:

the physical measurements include at least one of a temperature or a urine conductivity, and the chemical measurements include a concentration of at least one of sodium, potassium, chloride, lithium, pH, ammonia, urea, glucose, or lactate.

101. The urine collection system of example 99, further comprising:

a first plate including the urine inlet and the flow channel;

a second plate removably coupled to the first plate; and a sensing subassembly including the sensors, wherein the sensing subassembly is positioned between the first plate and the second plate.

102. The urine collection system of example 101 wherein:

the second plate includes a plurality of sensor slots, the sensing subassembly includes a body and a plurality of sensor tabs extending from the body, and the sensor tabs each include a corresponding one of the sensors.

103. The urine collection system of example 102 wherein the sensor slots are configured to receive the sensor tabs when the first plate is coupled to the second plate.

104. The urine collection system of any of examples 99-102 wherein the console includes one or more processors, wherein the urine cartridge includes an electrical connector in communication with individual ones of the plurality of sensors, and wherein the one or more processors are operably coupled to the electrical connector and configured to receive the sensor data therefrom.

105. The urine collection system of example 104 wherein the electrical connector is configured to releasably couple the urine cartridge to the console.

It will be apparent to those having skill in the art that changes may be made to the details of the above-described embodiments without departing from the underlying principles of the present technology. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Throughout this disclosure, the singular terms "a," "an," and "the" include plural referents unless the context clearly indicates otherwise. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

Unless otherwise indicated, all numbers expressing concentrations, temperatures, and other numerical values used in the specification and claims, are to be understood as being modified in all instances by the term "about." Accordingly, unless indicated to the contrary, the numerical parameters set forth in the following specification and attached claims are approximations that may vary depending upon the desired properties sought to be obtained by the present technology. When used, the term "about" refers to values within +/−10% of the stated value. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

We claim:

1. A flow cartridge for analyzing urine, the flow cartridge comprising:
   a first housing portion comprising—
      a urine inlet configured to receive urine from a patient;
      a urine outlet; and
      a channel fluidly coupled to and extending between the urine inlet and the urine outlet, wherein the channel includes sensing zones positioned between the urine inlet and the urine outlet;
   a second housing portion releasably coupled to the first housing portion;
   a sensing subassembly positioned at least partially between the first housing portion and the second housing portion, the sensing subassembly comprising:
      a body,
      a first sensor coupled to the body and positioned downstream from the urine inlet,
      a second sensor coupled to the body and positioned downstream from the first sensor, and
      a third sensor coupled to the body and positioned downstream from the second sensor;
      wherein each of the first, second, and third sensors is aligned with a corresponding one of the sensing zones and operable to generate sensor data based on urine flow through the corresponding sensing zone, and
      wherein the first sensor, the second sensor, and/or the third sensor are positioned at least partially within the channel; and
   a processor operably associated with the first, second, and third sensors and a pump of a fluid therapy system, wherein the processor is configured to:
      obtain the sensor data generated by the first, second, and third sensors; and
      cause the pump to administer, to the patient and based at least partially on the sensor data, a hydration fluid at a hydration fluid rate or a diuretic at a diuretic dosage rate.

2. The flow cartridge of claim 1, wherein:
   the first housing portion includes a first plate, and
   the second housing portion includes a second plate.

3. The flow cartridge of claim 2 wherein the sensing subassembly further comprises:
   a plurality of sensor tabs extending from the body,
   wherein the sensor tabs each include a corresponding one of the sensors.

4. The flow cartridge of claim 1 wherein the channel is a first channel, the sensing zones include first sensing zones, and the first, second, and third sensors are primary sensors operable to generate primary sensor data, the flow cartridge further comprising:
   a second channel fluidly coupled to the urine inlet,
   a plurality of secondary sensors downstream of the urine inlet and fluidly coupled to the second channel, and
   a plurality of second sensing zones fluidly coupled to the urine inlet, wherein the plurality of secondary sensors are each aligned with a corresponding one of the plurality of secondary sensing zones and operable to generate secondary sensor data based on urine flow through the corresponding secondary sensing zones.

5. The flow cartridge of claim 1, further comprising a flow control device transitionable between a first configuration in which the flow control device at least partially restricts urine flow, and a second configuration in which the flow control device enables urine flow.

6. The flow cartridge of claim 5 wherein the flow control device includes a pinch clamp or a stopcock.

7. The flow cartridge of claim 5 wherein the flow control device is positioned between individual ones of the sensing zones.

8. The flow cartridge of claim 5 wherein the sensing zones include a first sensing zone and a second sensing zone downstream of the first sensing zone, and wherein the flow control device is positioned between the first sensing zone and the second sensing zone.

9. The flow cartridge of claim 1, further comprising a plurality of flow control devices, wherein individual flow control devices are positioned between adjacent sensing zones.

10. The flow cartridge of claim 1 wherein the first sensor includes a first electrode, the second sensor includes a temperature sensor, and third sensor includes a second electrode.

11. The flow cartridge of claim 1 wherein the urine outlet is positioned at an elevation above the urine inlet.

12. A flow cartridge for analyzing urine, the flow cartridge comprising:
   a first housing portion comprising—
      a urine inlet configured to receive urine from a patient;
      a urine outlet;
      a first channel fluidly coupled to and extending between the urine inlet and the urine outlet, wherein the first channel includes first sensing zones positioned between the urine inlet and the urine outlet; and
      a second channel fluidly coupled to the urine inlet, wherein the second channel includes second sensing zones positioned downstream from the urine inlet, and wherein the first channel is arranged in parallel to the second channel;
   a second housing portion releasably coupled to the first housing portion; and
   a sensing subassembly positioned at least partially between the first housing portion and
      the second housing portion, the sensing subassembly comprising:
      a body;
      a plurality of primary sensors comprising—
         a first sensor coupled to the body and positioned downstream from the urine inlet,
         a second sensor coupled to the body and positioned downstream from the first sensor, and
         a third sensor coupled to the body and positioned downstream from the second sensor,
         wherein each of the first, second, and third sensors is aligned with a corresponding one of the sensing zones and operable to generate sensor data based on urine flow through the corresponding sensing zone, and wherein the first sensor, the second sensor, and/or the third sensor are positioned at least partially within the channel; and
      a plurality of secondary sensors downstream of the urine inlet and fluidly coupled to the second channel, wherein each of the plurality of secondary sensors are aligned with a corresponding one of the plurality of secondary sensing zones and operable to generate secondary sensor data based on urine flow through the corresponding secondary sensing zones.

13. The flow cartridge of claim 12 wherein the urine outlet is a first urine outlet, wherein the first housing portion comprises a second urine outlet spaced from the first urine outlet, and wherein the second fluid channel is fluidly coupled to the second urine outlet.

14. A flow cartridge for analyzing urine, the flow cartridge comprising:
   a first housing portion comprising—
      a urine inlet configured to receive a flow of urine; and
      a flow channel in fluid communication with the urine inlet and comprising a plurality of sensing zones, wherein the sensing zones are positioned in series relative to one another along a length of the flow channel; and
   a second housing portion releasably coupled to the first housing portion;
   a sensing subassembly positioned at least partially between the first housing portion and the second housing portion, the sensing subassembly comprising:
      a body; and
      a plurality of sensors coupled to the body and in fluid communication with the flow channel, wherein each of the sensors is aligned with a corresponding one of the sensing zones, wherein the sensors are each configured to measure a chemical parameter and/or a physical parameter of the urine, and wherein at least one of the plurality of sensors is positioned at least partially within the flow channel; and
   a processor operably associated with the sensing subassembly and a pump of a fluid therapy system, wherein the processor is configured to,
      obtain the chemical parameter and/or the physical parameter of the urine measured by one or more of the plurality of sensors; and
      cause the pump to administer, to a patient and based at least partially on the obtained chemical and/or physical parameter, a hydration fluid at a hydration fluid rate or a diuretic at a diuretic dosage rate.

15. The flow cartridge of claim 14 wherein:
   the physical parameter includes at least one of temperature or flow, and
   the chemical measurement includes a concentration at least one of sodium, potassium, chloride, lithium, pH, ammonia, urea, glucose, or lactate.

16. The flow cartridge of claim 14, wherein:
   the first housing portion comprises a first plate including the urine inlet and the flow channel; and
   the second housing portion comprises a second plate.

17. The flow cartridge of claim 16 wherein:
   the sensing subassembly further comprises a plurality of sensor tabs extending from the body, and
   the sensor tabs each include a corresponding one of the sensors.

18. The flow cartridge of claim 17 wherein the second plate includes a plurality of sensor slots, and wherein the sensor slots are configured to receive the sensor tabs when the first plate is coupled to the second plate.

19. The flow cartridge of claim 14 wherein, in operation, the flow channel directs the flow of urine upwardly in a direction at least partially against gravity.

20. The flow cartridge of claim 14 wherein the plurality of sensors comprise a first sensor configured to measure the chemical parameter and a second sensor configured to measure the physical parameter.

* * * * *